(12) United States Patent
Kasahara et al.

(10) Patent No.: US 6,576,463 B1
(45) Date of Patent: Jun. 10, 2003

(54) HYBRID VECTORS FOR GENE THERAPY

(75) Inventors: Noriyuki Kasahara, Los Angeles, CA (US); Collin Higo, Reno, NV (US); Harris Soifer, West Hills, CA (US); Kohnosuke Mitani, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/484,901

(22) Filed: Jan. 18, 2000

Related U.S. Application Data

(60) Provisional application No. 60/116,150, filed on Jan. 15, 1999.

(51) Int. Cl.$^7$ ...................... C12N 15/86; C12N 15/861; C12N 15/867; C12N 15/63; C12N 15/64

(52) U.S. Cl. ................. 435/320.1; 435/235.1; 435/69.1; 435/455; 435/456; 435/457; 424/93.1; 424/93.2; 424/93.6

(58) Field of Search ............... 435/320.1, 235.1, 435/69.1, 455, 456, 457; 424/93.1, 93.2, 93.6

(56) References Cited

U.S. PATENT DOCUMENTS

| 5,591,624 A | 1/1997 | Barber et al. ............ 435/240.2 |
| 6,156,497 A | 12/2000 | Kaleko ......................... 435/5 |

OTHER PUBLICATIONS

Bilbao, G., Feng, M., Rancourt, C., Jackson, W.H., Curiel, D.T., (Jul. 1997) Adenoviral/Retroviral Vector Chimeras: A Novel Strategy to Achieve High–Efficiency Stable Transduction In Vivo, The FASEB Journal, vol. 11, 624–634.

Boeck, J., (1997) LINEs and Alus–the polyA connection, Nature Genetics 16, 6–7.

Cannon P. M. et al., (1996), Murine leukemia virus–based Tat inducible LTR replacement vectors: a new system for anti–HIV gene therapy. J. Virol. 70, 8234–40.

Chakraborty, A. K. et al., (1994) Transmission of endogenous VL30 retrotransposons by helper cells used in gene therapy, Cancer Gene Ther. 1, 113–8.

Clemens, P. R. et al., (1996) In vivo muscle gene transfer of full–length dystrophin with an adenoviral vector that lacks all viral genes, Gene Ther. 3, 965–72.

Englehardt, J.F. et al. (1993). Direct gene transfer of human CFTR into human bronchial epithelia of xenografts with E1–deleted adenoviruses. Nat.Genet. 4, 27–34.

Feng, Q. et al. (1996). Human L1 retrotransposon encodes a conserved endonuclease required for retrotranposition. Cell 87, 905–16.

Fisher, K. J. et al. (1996). A novel adenovirus–adeno–associated virus hybrid vector that displays efficient rescue and delivery of the AAV genome. Hum. Gene Ther. 7, 2079–87.

Flotte, T. R. et al. (1993). Stable in vivo expression of the cystic fibrosis transmembrane conductance regulator with an adeno–associated virus vector. Proc. Natl. Acad. Sci. USA 90, 10613–7.

Flotte, T. R. et al. (1994) Adeno–associated virus vector gene expression occurs in nondividing cells in the absence of vector DNA integration. Am J Respir Cell. Mol. Biol. 11, 517–21.

Gao, G. P. et al. (1996). Biology of adenovirus vectors with E1 and E4 deletions for liver–directed gene therapy. J. Virol. 70, 8934–43.

Gueiros–Filho, F. J. and Beverly, S. M. (1997) Trans–kingdom transposition of the Drosophila element Mariner within the protozoan Leishmania. Science, 276: 1716–1719.

Haecker, S. E. et al.(1996). In vivo expression of full–length human dystrophin from adenoviral vectors deleted of all viral genes. Hum. Gen Ther. 7, 1907–14.

Halbert, C. L. et al. (1995). Adeno–associated virus vectors transduce primary cells much less efficiently than immortalized cells. J. Virol. 69, 1473–9.

Hattori, M. et al. (1986). L1 family of repetitive DNA sequences in primates may be derived from a sequence encoding a reverse transcriptase–related protein. Nature 321, 625–628.

Hodgson, C.P., Xu, G., Solaiman, F., Zink, M.A., (1997) Biosynthetic Retrovectoring Systems for Gene Therapy, Journal of Molecular Medicine, 75:249–258.

Hohjoh, H., and Singer, M. F. (1996). Cytoplasmic ribonucleoprotein complexes containing human LINE–1 protein and RNA. EMBO J. 15, 630–639.

Holmes, S. E., Singer, M. F., and Swergold, G. D. (1992). Studies on p40, the leucine zipper motif–containing protein encoded by the first open reading frame of an active human LINE–1 transposable element. J. Biol. Chem. 267, 19765–19768.

Hwang, L. H. S., and Gilboa, E. (1984). Expression of genes introduced into cells by retroviral infection is more efficient than that of genes introduced into cells by DNA transfection. J. Virol. 50, 417–424.

Ivics, Z. et al. (1997). Molecular reconstruction of Sleeping Beauty, a Tc1–like transposon from fish, and its transposition in human cells. Cell 91, 501–10.

Johnston, K.M., Jacoby, D., Pechan, P.A., Fraefel, C., Borghesani, P., Schuback, D., Dunn, R.J., Smith, F.I., Breakefield, X.O., (Feb. 10, 1997) HSC/AAV Hybrid Amplicon Vectors Extend Transgene Expression in Human Glioma Cells, Human Gene Therapy, 8:359–370.

(List continued on next page.)

*Primary Examiner*—David Guzo
(74) *Attorney, Agent, or Firm*—Bingham McCutchen LLP; Antoinette F. Konski

(57) ABSTRACT

The invention discloses hybrid vectors for delivering genes or other nucleic acids into mammalian cells. The hybrid vectors of the invention contain both a helper dependent adenoviral portion and a second portion derived from either a replication incompetent retrovirus or from a transposon. Such vectors provide efficient transduction of quiescent cells and provide for stable integration of the gene to be delivered.

52 Claims, 17 Drawing Sheets

OTHER PUBLICATIONS

Kaplan, J. M. et al. (1997). Characterization of factors involved in modulating persistence of transgene expression from recombinant adenovirus in the mouse lung. Hum. Gene Ther. 8, 45–56.

Kingsman, A.J., Burns. N.R., Layton, G.T., Adams. S.E., (1995) Yeast Retrotransposon Particles as Antigen Delivery Systems, Annals of the New York Academy of Sciences, vol. 754, 1–404, pp. 202–213.

Kochanek, S. et al. (1996). A new adenoviral vector: Replacement of all viral coding sequences with 28 kb of DNA independently expressing both full–length dystrophin and beta–galactosidase. Proc. Natl. Acad. Sci. USA 93, 5731–6.

Lieber, A. et al. (1996). Recombinant adenoviruses with large deletions generated by Cre–mediated excision exhibit different biological properties compared with first–generation vectors in vitro and in vivo. J. Virol. 70, 8944–60.

Lucher, L. (1995). Abortive adenovirus infection and host range determinants. In The Molecular Repertoire of Adenoviruses, W. Doerfler and P. Bohm, eds. (Berlin, Heidelberg, New York: Springer), pp. 119–152.

Mann, R. et al. (1983). Construction of a retrovirus packaging mutant and its use to produce helper–free defective retrovirus. Cell 33, 153–159.

Markowitz, D. et al. (1988). A safe packaging line for gene transfer: Separating viral genes on two different plasmids. J. Virol. 62, 1120–1124.

Miller, A. D., and Buttimore, C. (1986). Redesign of retrovirus packaging cell lines to avoid recombination leading to helper virus production. Mol. Cell. Biol. 6, 2895–2902.

Minakami, R. et al. (1992). Identification of an internal cis–element essential for the human L1 transcription and a nuclear factor(s) binding to the element. Nucl. Acids Res. 12, 3139–3145.

Mitani, K. et al. (1995A). Rescue, propagation, and partial purification of a helper virus–dependent adenovirus vector. Proc Natl Acad Sci U S A 92, 3854–8.

Mitani, K. et al. (1995B). Gene targeting in mouse embryonic stem cells with an adenoviral vector. Somat. Cell. Mol. Genet. 21, 221–231.

Moran, J. V. et al. (1996). High frequency retrotransposition in cultured mammalian cells. Cell 87, 917–27.

Mulligan, R. (1993). The basic science of gene therapy. Science 260, 926–932.

Parks, R. J. et al. (1996). A helper–dependent adenovirus vector system: removal of helper virus by Cre–mediated excision of the viral packaging signal. Proc. Natl. Acad. Sci. USA 93, 13565–70.

Parks, R. J., and Graham. F. L. (1997). A helper–dependent system for adenovirus vector production helps define a lower limit for efficient DNA packaging, J. Virol. 71, 3293–8.

Plasterk, R. H. (1996) The Tc1/mariner transposon family. Curr. Top. Microbiol. Immunol. 204, 125–43.

Plasterk, R.H. (1999) Resident aliens: the Tc1/mariner superfamily of transposable elements. Trends Genet. 15, 326–32.

Roessler, B. J. et al. (1995). Inhibition of interleukin–1–induced effects in synoviocytes transduced with the human IL–1 receptor antagonist cDNA using an adenoviral vector. Hum. Gene Ther. 6, 307–316.

Sassaman, D.M. et al.(1997). Many human L1 elements are capable of retrotransposition. Nat. Genet. 16, 37–43.

Savard, N., Cossett, F.L., Epstein, A.L., (May 1997) Defective Herpes Simplex Virus Type 1 Vectors Harboring gag, pol, and env Genes Can Be Used to Rescue Defective Retrovirus Vectors, Journal of Virology, 71(5), 4111–4117.

Scott, A. F. et al. (1987). Origin of the human L1 elements: proposed progenitor genes deduced from a consensus DNA sequence. Genomics 1, 113–125.

Singer, M. F. et al. (1993). LINE–1: a human transposable element. Gene 135, 183–188.

Soneoka, Y. et al. (1995). A transient three–plasmid expression system for the production of high titre retroviral vectors. Nucl. Acid Res. 23, 628–633.

Swergold, G. D. (1990). Identification, characterization, and cell specificity of a human LINE–1 promoter. Mol. Cell. Biol. 10, 6718–6729.

Thrasher, A. J., de Alwis, M., Casimir, C. M., Kinnon, C., Page, K., Lebkowski, J., Segal, A. W., and Levinsky, R. J. (1995). Generation of recombinant adeno–associated virus (rAAV) from an adenoviral vector and functional reconstitution of the NADPH–oxidase. Gene Ther. 2, 481–5.

Torrent, C. et al. (1994). Analytical study of rat retrotransposon VL30 RNA dimerization in vitro and packaging in murine leukemia virus. J. Mol. Biol. 240, 434–44.

Varmus, H. (1988). Retroviruses. Science 240, 1427–1435.

Weiss, R. et al. (1984). RNA Tumor Viruses: Molecular Biology of Tumor Viruses (Cold Spring Harbor, N.Y.: Cold Spring Harbor Laboratory) (Only front page and table of contents submitted).

Xiong, Y., and Eickbush, T. H. (1990). Origin and evolution of retroelements based upon their reverse transcriptase sequences. EMBO J. 9, 3353–3362.

Yang, Y. et al. (1995). Cellular and humoral immune responses to viral antigens create barriers to lung–directed gene therapy with recombinant adenoviruses. J. Virol. 69, 2004–15.

Yoshida, Y., Emi, N., Hamada, H., (1997) VSV–G–Pseudotyped Retroviral Packaging through Adenovirus–Mediated Inducible Gene Expression, Biochemical and Biophysical Research Communications, 232, 379–382.

Yoshimoto, T. et al. (1993). Identification of amino acid residues critical for infection with ecotropic murine leukemia retrovirus. J. Virol. 67, 1310–1314.

A. initial screen

B. after large scale culture growth

Figure 4
Day 2:
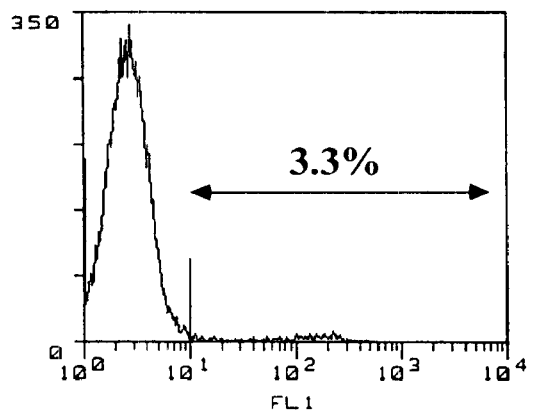
Day 4:
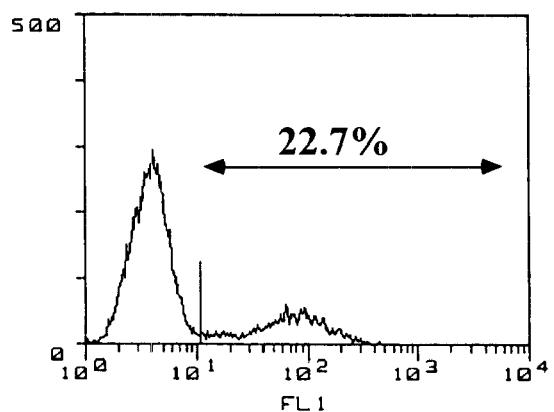
Day 7:
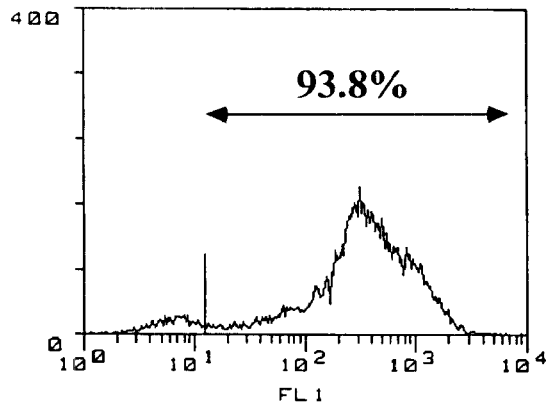

Figure 5

Stability of Recombinant gZD-GFP Virus Upon Passage in Cell Culture

- Day 4
- Day 7

Percent of cells transduced (by FACS analysis)

Infection number

Figure 6

Wild type virus infected DNA
Positive control

Infection number
1 2 3 4 5 6 7

AdLC8cluc

AdSTKCMVβ/AdLC8cluc

HYBRID VECTORS FOR GENE THERAPY

RELATED APPLICATION DATA

This application claims the benefit of provisional application Ser. No. 60/116,150 filed Jan. 15, 1999, the disclosure of which is incorporated by reference in its entirety.

GOVERNMENT SUPPORT

The government may have certain rights in this invention pursuant to grant no. 1R21DK054280-01 from the National Institutes of Health.

FIELD OF THE INVENTION

The invention relates to the field of medicine and in particular to vectors for delivery of nucleic acids into cells and to vectors useful for gene therapy.

BACKGROUND

One of the foremost obstacles to the practical implementation of human gene therapy is the lack of an optimal method for the direct delivery of therapeutic genes to quiescent tissues in vivo. A number of vector systems based on viral components have been developed; however, of these individual virus vector systems, none is optimal and each system displays significant drawbacks.

Retroviruses as vehicles for the delivery of genes into eukaryotic cells have several advantages (Hwang and Gilboa, 1984; Varmus, 1988): 1) gene transfer is relatively efficient; 2) stable integration into the host cell DNA is a natural part of the retroviral life cycle, and therefore the integrated provirus is passed on to all daughter cells, and continues to direct the nonlytic production of its encoded products; and 3) replication-defective vectors can be created by deletion of essential viral genes, which renders the vectors incapable of secondary infection (Mann et al., 1983; Markowitz et al., 1988; Miller and Buttimore, 1986). In spite of these advantages, retroviral gene transfer in its current form has several drawbacks. Most retroviral vectors in current use are traditionally based on Moloney murine leukemia virus (MLV), which requires cell division during infection so that the nucleocapsid complex can gain access to the host cell genome, and hence cannot infect non-dividing cells (Mulligan, 1993; Varmus, 1988). Many cell types are considered to be largely quiescent in vivo, and furthermore, most retroviral vectors are produced from packaging cells at titers on the order of only $10^{6-7}$ colony-forming units (cfu) per ml, which is barely adequate for transduction in vivo. Therefore, retroviral gene transfer in vivo is inefficient, and the traditional approach which has been adopted for retroviral vectors has been to transduce primary cells in culture by the ex vivo method, followed by re-implantation of the transduced cells. This approach requires surgical acquisition, isolation, and culture of autologous cells, and thus is labor-intensive and invasive, and limits the scope of ex vivo retroviral gene transfer to those cell types that can be readily accessed, maintained and manipulated in culture, and reimplanted, e.g., hematopoietic cells, skin fibroblasts, and hepatocytes.

On the other hand, adenoviral vectors have been shown to efficiently infect many cells types in vivo by direct injection. However, as the adenoviral vector remains episomal and does not integrate into the host cell genome, transgene expression is transient. The utility of adenoviral vectors is further limited by cellular and humoral immune responses against wild type adenovirus gene products, which appear to be expressed at low levels in the transduced cells due to "leaky" expression despite deletion of the E1 regulatory region (Engelhardt et al., 1993; Yang et al., 1995). Once sensitized, a neutralizing antibody response usually precludes repeat administration by the same vector, and adenovirus-infected cells are soon eliminated by cytotoxic T lymphocytes after transduction (Roessler et al., 1995; Yang et al., 1995). Thus, neither type of virus vector can achieve efficient and long term transduction by direct injection in vivo.

Another virus vector which has been considered is the adeno-associated virus (AAV) (Flotte et al., 1993). AAV was initially thought to be advantageous because it appeared to efficiently infect non-dividing cells (Flotte et al., 1994), and would also undergo site-specific integration into the host cell genome, resulting in long term transduction. However, although these do appear to be attributes of wild type AAV, it seems that these characteristics may not be associated with replication-defective AAV vectors, from which the AAV structural genes, especially the rep gene, have been deleted (Halbert et al., 1995). Other disadvantages of the AAV system have been the limited packaging capacity, only about 4 kilobases, of the vector, and the difficulty of making high titer AAV stocks.

Retrotransposons are mobile genetic elements that insert into new genomic locations by a mechanism that involves reverse transcription of an RNA intermediate. Among the most well-characterized human retrotransposons are L1 elements or LINEs (long interspersed nuclear elements); these non-LTR elements are present in approximately 100,000 copies in the human genome, although 97% of these are functionally inactive due to truncations and rearrangements, and of the remaining 3000 or so full length L1 elements (Singer et al., 1993), it has been estimated that only about 1.5–2.5%, i.e., 30 to 60 copies, are active in retrotransposition (Sassaman et al., 1997). A 6 kb L1 consensus sequence has been derived by sequence analysis of multiple elements (Scott et al., 1987), containing a 5' untranslated region with an internal promoter (Minakami et al., 1992; Swergold, 1990), two non-overlapping reading frames (ORF 1 and ORF 2), a 3' untranslated region and 3' polyadenylated tail; ORF 1 encodes a 40 kD nucleic acid binding protein that co-localizes with L1 mRNA in a cytoplasmic complex (Hohjoh and Singer, 1996; Holmes et al., 1992), while ORF 2 encodes a protein with reverse transcriptase (RT) activity (Hattori et al., 1986; Xiong and Eickbush, 1990) and an N-terminal endonuclease (EN) domain (Feng et al., 1996). Recently, it has been demonstrated that a reporter cassette, with a selectable marker gene driven by the SV40 promoter, can be inserted in reverse orientation into the 3' untranslated region of L1 elements, and when transfected into cells as an EBNA/oriP-containing episomal plasmid, this system can be used to detect retrotransposition events (Moran et al., 1996; Sassaman et al., 1997). The human L1/reporter element was also active in mouse fibroblasts, suggesting that cellular factors involved in retrotransposition are conserved (Moran et al., 1996). Furthermore, this system was used to characterize novel human L1 sequences that were screened from a genomic library; one of these, L1.3, retrotransposed at a considerably higher frequency, about 1 retrotransposition event scored per 150 cells containing the episomal plasmid (Sassaman et al., 1997). In fact, the actual frequency is probably even higher, as the assay system scored only retrotransposition events occurring in cells that had been pre-selected for the presence of the full length episomal plasmid. Interestingly, it was found that the promoter in the 5' untranslated region could be replaced with the CMV promoter without significantly affecting the retrotransposition frequency, and that the 3' untranslated region could be completely deleted without any deleterious effect. When some of the integration sites of the L1/reporter element were cloned and the 5' junctions sequenced, the elements were found to have been variably truncated 5' of the selectable marker gene. This results in an integrated element that is presumably incapable of further retrotransposition, as: 1) the 5' promoter is truncated, thus no mRNA intermediate would be transcribed in the forward orientation; 2) the essential ORF (at least ORF 1, and in some cases ORF 2 also) functions are deleted; and 3) even if the ORF 1 and ORF 2 gene products were to be provided in trans, it has been suggested that the retrotransposition process might be designed to ensure that only mRNA that is in cis with the ORFs is preferentially retrotransposed, perhaps by interaction of the nascent ORF 2 protein with the polyA tail of its own transcript during translation (Boeke, 1997).

Although use of retrotransposons as gene delivery vehicles has been previously suggested (Hodgson et al., 1997; Kingsman et al., 1995), and in fact retrotransposons such as rat VL30 elements have been found capable of being packaged and transmitted by MLV (Chakraborty et al., 1994; Torrent et al., 1994), thus far the efficiency of delivering retrotransposon-encoded sequences to target cells has been the rate-limiting step.

Thus, heretofore there has been no optimal method for direct gene transfer and permanent transduction of quiescent tissues in vivo. Although retroviral gene transfer is currently one of the most commonly used methods for delivery of therapeutic genes, it suffers from problems such as relatively low titers and inability to transduce non-dividing cells; conversely, although adenoviral vectors and non-viral lipid-DNA conjugate vectors offer advantages such as high titers, and the ability to transduce quiescent cells, neither is capable of efficient integration or permanent transduction. Furthermore, other integrating elements such as retrotransposons and AAV have been modified for use as vectors, but these systems suffer from the lack of an adequate delivery system or simple methods for production of high titer preparations.

A different approach that has been taken in the design of vectors suitable for gene therapy is the combination of elements from distinct viral vectors. Insertion of retroviral structural genes into Herpes simplex virus (HSV) (Savard et al., 1997) has been described. In this case, only retroviral structural genes were inserted into the HSV carrier, which was used to mobilize a retroviral vector sequence already integrated into an indicator cell line.

Insertion of retroviral structural genes and vector constructs into adenovirus (Bilbao et al., 1997) has been reported; however, retroviral structural genes and retroviral vector constructs had to be inserted separately into standard E1-deleted adenovirus vectors (Bilbao et al., 1997), reflecting the limited cloning capacity, about 7 kb, of the adenovirus vectors used. Adenoviruses carrying the retrovirus structural genes and those carrying the retroviral vector constructs were mixed together to achieve co-infection by both types of adenovirus carriers and thus co-expression of retroviral structural gene and vector constructs, resulting in the secondary production of fully assembled, functional retroviral vectors.

Insertion of retroviral structural gene sequences into adenoviral vectors to produce a hybrid construct previously has also been described as a means to achieve efficient transient expression of packaging proteins, particularly for high titer production of vectors pseudotyped with the VSV-G envelope protein, which is toxic to cells and is usually difficult to express in stable packaging cell lines without tight regulation (Yoshida et al., 1997). Other groups have reported similar approaches for efficient production of AAV vectors, by insertion of AAV structural gene or vector sequences into adenovirus-based hybrid expression systems (Fisher et al., 1996; Thrasher et al., 1995). There has been one report describing the production of hybrid vectors consisting of AAV sequences inserted into a Herpes simplex virus (HSV) amplicon for use as a novel gene delivery vehicle (Johnston et al., 1997). Nevertheless, the applicability of retrovirus sequences as inserts within the context of a larger heterologous virus as a vector for gene delivery was heretofore unknown.

Recently, helper-dependent adenoviral vector systems have been developed; the first such system was originally reported by one of us in 1995 (Mitani et al., 1995) and consisted of a reporter gene cassette inserted in an adenoviral genome that had been deleted of many of its structural elements, retaining the inverted terminal repeat (ITR) and packaging signal sequences. Subsequently, a 28 kb vector DNA containing the full length dystrophin gene, with only 360 bp of adenoviral DNA including the replication origin and the packaging signal, was successfully rescued and propagated in adenoviral virions in the presence of helper virus (Clemens et al., 1996; Kochanek et al., 1996). In this system, all the coding sequences that could be toxic or immunogenic to the host were thus removed from the vector DNA. Although some contaminating helper adenovirus is still present in preparations of helper-dependent vectors, cesium chloride gradient separation has allowed purification of the helper-dependent vectors with residual helper virus present at levels of less than 1% (Kochanek et al., 1996; Mitani et al., 1995), and recently reported refinements in the packaging system appear to reduce the level of helper virus contamination even further, to less than 0.01% (Lieber et al., 1996; Parks et al., 1996).

Another advantage of this system is expanded cloning capacity (up to 38 kb) of foreign DNA into the vector. Interestingly, the minimal packaging size requirement was previously defined as 25 kb or so (Mitani et al., 1995); however, it has recently been shown that smaller vector constructs can also be packaged if concatemerization of the vector sequence occurs, resulting in a multimeric size that is within the 27 to 38 kb packageable size range (Parks and Graham, 1997). This expanded capacity is quite advantageous in the case of large genes; as mentioned above, helper-dependent adenoviral vectors recently have been used to deliver the full-length (14 kb) dystrophin gene into skeletal muscle in cell culture and in vivo (Clemens et al., 1996; Haecker et al., 1996). It is noteworthy that the helper-dependent dystrophin adenovectors appear to elicit no inflammatory reaction in vivo. This lack of inflammatory reaction correlated with prolonged expression of the dystrophin transgene, although there have been reports of both shortened and lengthened transgene expression with other deleted adenovector systems (Gao et al., 1996; Kaplan et al., 1997; Lieber et al., 1996). In spite of the success with helper-dependent adenoviral vectors, this approach is still limited by the inherent lack of stable integration.

The present invention incorporates integrating elements such as retrovirus and retrotransposon vectors as inserts within the context of high capacity helper-dependent adenovirus vectors, and thus constitutes a novel type of hybrid vector system that has not previously been described in the literature.

SUMMARY

The invention provides hybrid vectors suitable for the delivery of genetic material or nucleic acid molecules into a cell. The hybrid vectors comprise an adenoviral capsid that delivers a helper-dependent nucleic acid molecule encoding an adenoviral region and other inserted heterologous vector elements such as a retroviral region or transposon region.

The adenovirus capsid that encoats the nucleic acid molecule is provided by a helper aderiovirus. The helper adenovirus can be any adenovirus or adenovirus vector, derived from any serotype, that can provide adenovirus early and late proteins necessary for replication and packaging of the helper-dependent nucleic acid molecule, which is itself incapable of being replicated or packaged in eukaryotic cells in the absence of the helper adenovirus.

The adenovirus region of the nucleic acid molecule of the hybrid vector comprises a helper-dependent or "gutted" adenoviral vector. Such vectors lack genes necessary for replication and packaging of the adenovirus and are unable to replicable in the absence of the helper adenovirus that supplies the necessary adenoviral structural elements. The adenoviral region therefore can substantially lack nucleic acid sequences encoding adenoviral structural genes. Nucleic acid molecules of the hybrid vectors contain within the adenoviral region a pair of adenoviral inverted terminal repeat sequences as well as a packaging signal from the adenovirus. The elements of the adenoviral region can be those found in any adenovirus, substantially similar sequences, or combinations of such sequences. In one embodiment, adenoviral regions have sequences substantially similar to those found, for example, in adenovirus serotype 2. In another embodiment, adenoviral regions have sequences substantially similar to those found in adenovirus serotype 5.

The hybrid vector system of the invention transduces cells by a two stage mechanism. In the first adenoviral stage, the inserted vector elements, included in the helper-dependent nucleic acid molecule to be delivered, will be carried by the adenoviral capsid, to then be expressed in the target cells and thereby direct the production of the second stage vectors.

In one embodiment, the inserted vector elements of the invention also contain a second stage retroviral region. The retroviral region has sequences that are substantially similar to those of any suitable retrovirus or retroviral vector or vectors including, but not limited to, oncoretrovirus and lentivirus vectors. A preferred retroviral region contains a packaging component, which consists of virus structural gene sequences substantially similar to the gag, pol and env genes from a retrovirus or from different retroviruses. The retroviral region of the hybrid vector is preferably replication incompetent. Such a retroviral region therefore contains a packaging component that lacks the retroviral packaging signal and hence substantially lacks the ability for the sequences in the packaging component itself to be packaged by its encoded retrovirus proteins. The packaging component of the retroviral region also preferably contains one or more promoters that enhance the expression of the retroviral structural genes included in the construct. The promoter(s) can be one or more retroviral long terminal repeats (LTR) flanking the retroviral structural genes. The promoter(s) also can be heterologous viral promoter(s) such as the SV40 promoter or the CMV promoter, or any other promoter that performs this function, including, for example, tissue specific promoters.

The second stage retroviral region of the inserted vector elements encoded within the nucleic acid molecule of the hybrid vector also contains a retroviral gene transfer component that is capable of being packaged by the retroviral structural proteins encoded by the packaging component of the retroviral region. The sequences encoding the retroviral gene transfer component are preferably contained between two flanking retroviral LTR sequences, and also contain a retroviral packaging signal sequence and any nucleic acid sequence of interest. The flanking LTRs can be those of a single retrovirus. In a preferred embodiment the first and second LTRs have different sequences. Such LTR sequences can be substantially similar to those of different retroviruses or those from a single retrovirus that have been altered to possess minimal sequence homology while maintaining functionality. The packaging signal sequence comprises the cis-acting elements that enable the transcribed retroviral gene transfer component to be packaged by the retroviral structural proteins encoded by the packaging component. Nucleic acid sequences of interest can be any nucleic acid molecule for which delivery is desired, including nucleic acids encoding, for example, genes, cDNAs and various RNA species including, for example, ribozymes, antisense sequences and structural RNAs.

In the secondary stage, the newly expressed retroviral vector elements of the hybrid vector will result in a replication-defective retrovirus vector particle, containing the retroviral structural proteins of the packaging component and the packaged RNA transcript of the retroviral gene transfer component, that will stably transduce additional adjacent cells.

The transposon region has a sequence substantially similar to that of any known retrotransposon or DNA transposon, and can also contain heterologous elements within the transposon region. Such transposons permanently integrate into the genome of the initially transduced cells, and the heterologous elements are contained within the transposon regions, and hence will also be integrated during this process. The heterologous elements can also contain promoter, polyadenylation signal, and/or any other sequences necessary for expression of an operably linked sequence of interest also contained within the heterologous element.

BRIEF DESCRIPTION OF THE DRAWINGS

FIG. 2A shows the results just after the initial mini-screen. FIG. 2B shows the results after amplification of the plasmids in large scale bacterial cultures.

FIG. 4 shows a fluorescence-activated cell sorter (FACS) analysis of GFP expression from RCR vector spread at various time points after initial infection.

FIG. 5 shows a fluorescence-activated cell sorter (FACS) analysis of GFP expression and retrovirus propagation after 8 serial passages.

FIG. 6 shows a Southern blot analysis of GFP-containing RCR vector at various time points after initial infection.

FIG. 19A shows the results of a PCR analysis of individual clones using neoR-specific primers. Lane 1 shows a 1 kb ladder; Lanes 2–6 are individual $G418_R$ clones; lane 7 is a HeLa cell negative control; and lane 8 is an unspliced vector control. FIG. 19B shows a Southern blot analysis of individual clones probes with aneoR fragment: lanes 1–3 are individual $G418_R$ clones; lane C is a negative HeLa DNA control; and lane L is a linear vector control.

DETAILED DESCRIPTION

Definitions

Figure 1:
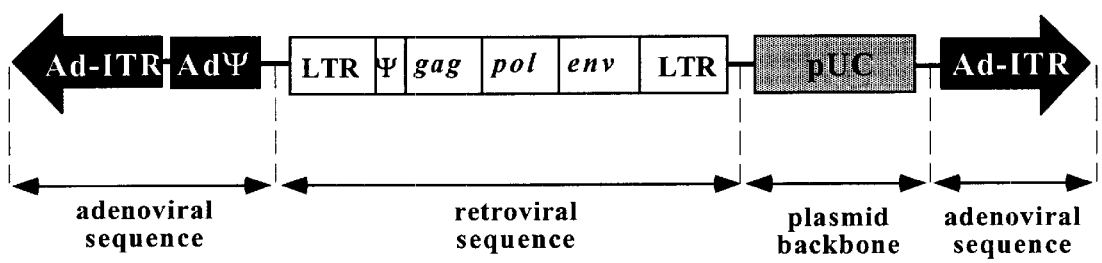
FIG. 1 illustrates the retrovirus-adenovirus hybrid vector construct RAd-ZAP.

The term "operably linked" refers to two or more nucleic acid sequences that are positioned such that a functional relationship is maintained. Operably linked sequences can be adjacent, or distal to one another in a nucleic acid molecule. For example, a promoter may function to regulate expression of a gene though it is located distally from the gene.

The term "region" as used herein defines a portion of a nucleic acid molecule or nucleic acid sequence that has a common function or a common origin, i.e. regions are derived from the same class of virus. Because a region can be interrupted, for example, by a nucleic acid molecule to be delivered or by another region, regions encompass contiguous and non-contiguous nucleic acid sequences. "Substantially similar" as used herein describes a relationship between nucleic acid sequences wherein the sequences are at least about 50% identical, preferably 70% identical and more preferably 90% identical when the sequences are aligned such that identical residues are maximized. A substantially similar sequence includes one in which codons have been changed to facilitate expression in a particular host organism. Codon usage preferences are known to one of skill in the art of molecular biology.

Variants of known sequences coding for proteins are preferred that result in the substitution of amino acids with amino acid residues with similar characteristics. A preferred substitution for aspartic acid, for example, would be another acidic residue, i.e. glutamic acid. One of skill in the can determine similar preferred substitutions for hydrophobic, basic, large and small amino acid groups.

Adenoviral Vectors

Hybrid vectors are provided that contain both adenoviral regions and secondary elements such as retroviral regions or transposon regions. Such hybrid vectors are novel systems for the delivery of genetic material or nucleic acid molecules to a cell. Such vectors can be efficient enough for direct in vivo application and can be capable of long term transduction. The term vector can be used to describe both the nucleic acid component of a vector as well as nucelic acids packaged as viral particles.

In this hybrid virus system, an adenoviral vector delivers the secondary vector elements into the host nuclei. As described above, adenoviral vectors can infect non-dividing cells efficiently and can be prepared as a high titer stock. Thus, this system is currently considered as the most efficient in vivo gene delivery system. To circumvent the immunogenicity problem of first-generation (E1-deleted) adenoviral vectors, which result in rapid clearance of vector-transduced cells, a preferred adenoviral region for inclusion in the hybrid vector is a helper-dependent adenoviral vector. Not only is the immunogenicity minimized with this system, but also large or multiple inserts can be delivered via this system. Thus, in the present invention, we utilize the machinery of retroviruses and retrotransposons, delivered in the context of a helper-dependent adenovirus vector, to achieve stable integration and permanent transduction.

The adenovirus region of the hybrid vector is a helper-dependent or "gutted" adenoviral vector. Such vectors lack genes necessary for replication of the adenovirus and are unable to replicate in the absence of a helper virus that supplies necessary adenoviral structural genes. The adenoviral region substantially lacks nucleic acids encoding adenoviral structural genes. Hybrid vectors contain within the adenoviral region a first and second adenoviral inverted terminal repeat sequence as well as a packaging signal from the adenovirus. The elements of the adenoviral region can be those found in any adenovirus, substantially similar sequences, or combinations of such sequences. In one embodiment, adenoviral regions have sequences substantially similar to those found, for example in adenovirus serotype 2. In another embodiment, adenoviral regions have sequences substantially similar to adenovirus serotype 5. The adenoviral inverted terminal repeats (ITRs) can be organized in any functional orientation within the hybrid vector. For example, the ITRs can be organized in a head to head or in a tail to tail orientation. ITRs preferably surround the second stage insert. The adenoviral packaging signal is preferably located adjacent to one of the ITR sequences.

Retroviruses as Second Stage Inserts

Retroviral vectors can be used as the secondary element in our hybrid system, both retroviral structural genes and retroviral vector elements can be contained within the same adenovirus carrier, thus enhancing the efficiency of second-stage retrovirus vector production.

The retroviral region is preferably located within the region between the first and second adenoviral inverted terminal repeat such that said retroviral region can be packaged into an adenoviral virion in the presence of an adenoviral helper virus.

Retroviral regions of the hybrid vector have a packaging component containing sequences encoding one or more retroviral structural genes. Such genes include, for example the gag, pol and env proteins. These proteins are necessary for formation of functional retroviral particles capable of infecting cells adjacent to those initially infected by the adenoviral mechanism. The retroviral region preferably directs the production of a replication incompetent retroviral vector. The retroviral structural genes of the retroviral region can be located adjacent to one another or can be separated from one another within the hybrid vector. The gag, pol, and env sequences can be those of any suitable retrovirus or retroviral vector or combinations thereof. In one embodiment, a retroviral region includes the gag and pol sequences. In another embodiment, the hybrid vector includes the gag, pol, and env sequences. The env sequence is the predominant determinant of the host range of the second stage retroviral particles produced. env sequences can be chosen from retroviruses that target a specific cell type, or can be those known to one of skill in the art that have been engineered to target a selected target cell type. The retroviral region also preferably contains a promoter sequence operably linked to said retroviral structural genes. The promoter sequence can be any promoter sequence capable of enhancing expression of the retroviral sequences within the initial host cell. The promoter can be, for example, an SV40 promoter or a CMV promoter. The packaging component of the retroviral region preferably lacks a packaging signal, so transcripts arising from the component itself cannot be packaged into a retroviral particle by the structural proteins that it encodes.

Retroviral regions of the hybrid vectors have sequences that are substantially similar to those of any retroviral vector or retrovirus including, but not limited to, lentiviruses, such as human immunodeficiency virus (HIV), simian immunodeficiency virus (SIV), feline immunodeficiency virus (FIV), equine infectious anemia virus (EIAV), and caprine arthritis encephalitis virus (CAEV), avian retroviruses such as spleen necrosis virus (SNV) and Rous sarcoma virus (RSV), and oncoretroviruses such as Moloney murine leukemia virus (MLV), murine sarcoma virus (MSV), and feline leukemia virus (FeLV). Many retroviruses suitable for use with the invention are described in J. Coffin, S. Hughes and H. Varmus. 1997. *Retroviruses*. Cold Spring Harbor Press, Cold Spring Harbor, N.Y.

The retroviral region also contains a retroviral gene transfer component. The retroviral gene transfer component is a vector derived from any retroviral genome including, for example, the long terminal repeats (LTRs) of a suitable retrovirus that flank a heterologous sequence of interest and also containing a packaging signal sequence that allows the transcribed gene transfer component RNA to be packaged by the structural proteins encoded by the packaging component, resulting in the formation of second stage retroviral particles after initial adenoviral infection of a cell.

Transposon Elements as Second Stage Inserts

Hybrid vectors can also contain a transposon region. A transposon region can be any suitable DNA transposon or retrotransposon sequence or a sequence substantially similar to that of any known retrotransposon or DNA transposon. Such transposons permanently integrate into the genome of the initially transduced cells. Retrotransposon-derived transposon regions contain a sequence encoding a capsid-like protein and a sequence encoding a reverse transcriptase. The retrotransposon-derived transposon region also contains a promoter sequence operably linked to the capsid-protein encoding sequence and to the reverse-transcriptase encoding sequence. DNA transposon-derived transposon regions contain inverted or direct repeat sequences flanking the sequence to be integrated, and also contain sequences encoding a transposase which catalyzes the excision of the transposon from its original location and promotes its re-integration elsewhere, and a promoter sequence operably linked to the transposase encoding sequence. The transposon region of the hybrid vector can also contain a heterologous element that encodes a sequence of interest to be integrated into the host cell genome along with the transposon during the process of transposon integration. The sequence of interest can also be operably linked to a promoter, polyadenylation signal, and other sequences within the heterologous element in order to facilitate its expression in the host cell.

In one embodiment, the transposon regions is derived from a retrotransposon vector which is an L1 retrotransposon containing a heterologous element containing a reporter gene expression cassette. By insertion of such an L1/reporter element into the helper-dependent adenovirus system, the retroelement can be efficiently delivered to the adenovirus-transduced target cells, and subsequently retrotransposed and stably integrated into the DNA of these same cells. Although the frequency of retrotransposition may be as low as 1 in 150 of the adenovirus-transduced cells, since adenovirus titers can reach as high as $10^{10}$ to $10^{11}$ pfu per ml, this will still result in an integration frequency that compares favorably with that of retroviral titers. In fact, in addition to the high transduction efficiency achievable with adenovirus vectors, the adenoviral transgene copy number increases with increasing multiplicity of infection (MOI), and so the level of retrotransposon expression per cell may increase as well, leading to higher frequencies of retrotransposition. Furthermore, as the integrated L1 elements will often end up with truncated ORF 1 and ORF 2 sequences at their 5' ends (Moran et al., 1996), we suggest that this system is relatively safe, and that there will be little chance of promiscuous recurrent transposition leading to unacceptable frequencies of insertional mutagenesis. An advantage of such a retrotransposon-adenovirus hybrid vector system is that the same cell that was originally transduced by the first-stage adenovirus vector will itself be permanently transduced by the second-stage L1 retrotransposon vector, unlike the retrovirus-adenovirus hybrid vector system in which the initially transduced cell serves as a packaging intermediate for production of the second-stage retroviruses that then permanently transduce adjacent cells. An additional potential advantage is that the L1 elements are normally present endogenously in all human cells, thus in combination with the helper-dependent adenovirus vector which is itself deleted of all the adenoviral structural genes, this may provide a high titer adenovirus-based system that is capable of stable integration into the host cell genome, yet will not induce a Class I immune response directed against the vector itself.

It should be noted in this context that the present invention can be practiced not only with retrotransposon elements as the secondary inserts (described in detail in Examples 6 and 12–14), but, in another embodiment, with DNA transposon elements. In the case of the latter, the transposon vector element is released from the first stage adenoviral genome and inserted into the target cell chromosome by a simple "cut-and-paste" mechanism encoded by the transposon, structural genes. DNA transposons suitable for incoparation into hybrid vectors include those substantially similar to the Tc1 family of DNA transposons (Plasterk, R. H., 1996; Plasterk, R. H., 1999). Such transposons include those with sequences substantially similar to naturally occuring transposons such as Mariner (Gueiros-Filho and Beverly, 1997) as well as those substantially similar to natural sequences such as Sleeping Beauty (Ivics, Z. et al., 1997).

Genetic Material

The vectors of the invention are suitable for the delivery of any genetic material or nucleic acid molecule of interest to a cell. The hybrid vectors can contain a nucleic acid sequence to be delivered to a cell. For example, a gene or DNA sequence encoding a protein product can be such that expression of said gene relieves a deficiency in the target cell or within the organism. The nucleic acid molecule to be delivered is not limited to genes and protein encoding sequences. Other sequences suitable for delivery include RNA sequences such as structural RNA molecules, RNA molecules designed to bind to particular cellular components, e.g. aptamers, RNA molecules that possess catalytic activity (ribozymes) and RNA molecules that bind to specific mRNA molecules (antisense molecules).

For optimization and laboratory usage, a marker gene is the preferred genetic material to be included in hybrid vector. A marker gene is detectable by any number of techniques, including by fluorescence detection, calorimetric detection or immunologic detection. One of skill in the art can determine any number of suitable marker genes for use with the invention. Particularly preferred marker genes are expressed as fluorescent products such as green fluorescent protein and variants thereof.

Cells

Cells of the invention include cells from any organism. Preferred cells of the invention are animal cells. More preferred cells of the invention are mammalian cells. Vectors of the invention can be used to infect cells in vivo or ex vivo. Cells encompasses cultured cells as well as cells within an organism. Suitable cells can be, for example, human, cow, horse, pig, rabbit, rat or mouse cells. Choice of suitable vector components as described herein can be used to determine the host range of the hybrid vectors.

General Techniques

The construction of vectors from the elements or regions described is within the ability of one skilled in the art of molecular biology. Hybrid vectors of the invention are often constructed in the form of plasmids that are linearized before infection of initial target cells. General molecular biology techniques may be used, such as those described in Sambrook, J. et al., 1989, Molecular Cloning: A Laboratory Manual, Cold Spring Harbor Laboratory, NY; or Ausubel, F. M. et al., 1989, Current Protocols in Molecular Biology, John Wiley & Sons, New York N.Y., both of which are incorporated herein by reference in their entirety. More specifically, manipulations of viruses and of viral vectors is described in, for example, Hitt, M. Human adenovirus vectors for gene transfer into mammalian cells. Adv Pharmacol. 1997; 40:137–206; Becker, T. C. et al. Use of recombinant adenovirus for metabolic engineering of mammalian cells. Methods Cell Biol. 1994;43 Pt A:161–89, and Graham, F. L. and Prevec L. Manipulation of adenovirus vectors. Molecular Biotechnology 1995; 3:207–220.

Helper Adenoviruses

Because the hybrid vectors of the invention are helper-dependent, it is necessary to use a helper adenovirus to package the adenovirus particle. A number of helper adenovirus vectors are known. A preferred helper adenovirus is defective in one or more genes and/or other sequences or has been engineered such that it is unlikely to contaminate the prepared adenovirus particles encoded by the hybrid vectors described herein. A particularly preferred helper adenovirus system is one that uses the Cre-Lox system described herein.

EXAMPLES

Example 1

Construction of Retrovirus-adenovirus Hybrid Vector Constructs

We first constructed the simplest form of retrovirus-adenovirus hybrid vector by inserting a replication-competent wild type retrovirus genome within a completely "gutted" helper-dependent adenovirus construct. The wild type ecotropic Moloney murine leukemia virus (MLV) proviral genome, along with some genomic rat sequences flanking the MLV long terminal repeats (LTRs), was excised from the plasmid pZAP (generously provided by Dr. J. Young, Harvard) and inserted into the plasmid pUC-ITR, which contains the left and right inverted terminal repeats (ITRs) cloned into pUC19 in a head-to-head configuration along with the packaging ($\psi$) sequences of adenovirus serotype 5. The resultant vector is shown schematically in FIG. 1.

While this construct was initially made and confirmed by restriction digest of plasmid mini-preps, when we tried to grow large scale cultures for transfection experiments, the construct proved to be unstable, rapidly yielding a smaller band that was suspected to be a rearranged or deleted form. This occurred in any *E. coli* host strain that was tried, including HB 101 (recA$^-$) and SURE (recBCD$^-$) cells, under any conditions tried, including slower growth on solid media at lower temperatures with or without ampicillin selection pressure, which we have often found to enable replication of rearrangement-prone plasmids.

Figure 2:
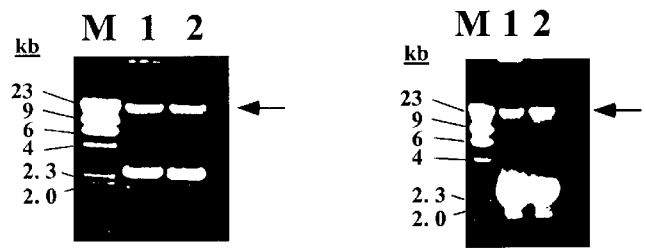
FIG. 2 shows the instability of retrovirus/adenovirus hybrid vector construct pRAd-ZAP. Lane M: Lambda/Hind III marker lane. Lanes 1 and 2 show two independent colonies of transformed bacteria HB101 that were positive on initial screening. The arrow points to the hybrid vector construct.

The band in FIG. 2B at about 2.5 kb is seen to increase in intensity relative to the vector plasmid, suggesting that the plasmid is unstable, and that deletion mutations are occurring with time.

Example 2

Construction of Retrovirus-adenovirus Hybrid Vector Constructs with Modified Repeat Sequences This example describes an improved construct in which the retroviral LTR was altered to provide a stable construct for large scale preparation.

As both the retrovirus as well as the adenovirus sequences were each stable within their respective plasmids, it seemed likely that the combining of four repeat sequences (i.e., 2 retrovirus LTRs and 2 adenovirus ITRs) may have contributed to the instability of the plasmid. Thus, we re-cloned the wild type MLV genome from pZAP so that the 5' LTR of MLV was replaced with that of murine sarcoma virus (MSV). MLV and MSV differ slightly in their LTR sequences and it was presumed that this would add some stability to the construct. In addition, we also inserted an internal ribosome entry site (IRES)-green fluorescent protein (GFP) marker gene cassette just downstream from the env gene stop codon and before the 3' LTR. This results in a polycistronic transcript that couples expression of the *Aequorea victoria* GFP to that of the retroviral envelope, enabling us to easily detect infection events.

Figure 3:
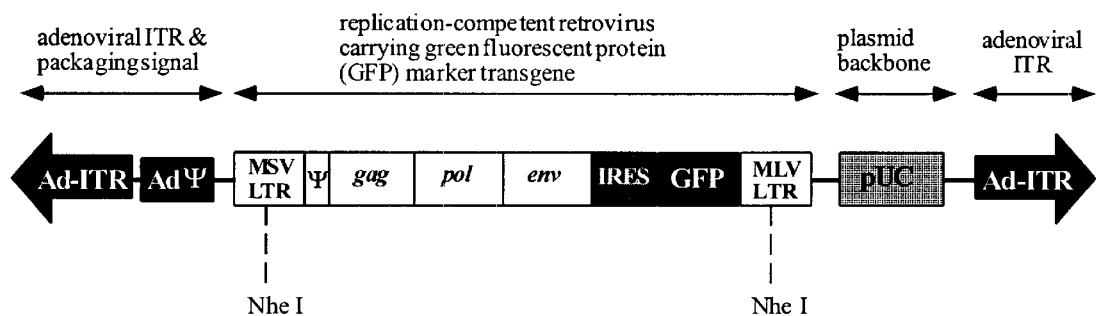
FIG. 3 shows the retrovirus-adenovirus hybrid vector construct RAd-g1ZDGFP.

The resultant retrovirus-adenovirus hybrid vector construct, RAd-g1ZDGFP, is shown in FIG. 3. This construct therefore contains one copy of a full length MLV retrovirus (with a 5' MLV LTR) that carries an additional marker transgene, GFP. We have confirmed that this retrovirus vector is fully replication competent and is capable of serial propagation in NIH3T3 cells, and that the addition of the transgene does not compromise packaging capability or titer. The GFP transgene is transmitted along with the virus and spread of GFP expression concomitant with virus replication can be detected and quantified by fluorescence-activated cell sorter (FACS) assay. Even without selection for retention of the GFP transgene, this genome configuration appears to remain stable throughout this interval, perhaps because transgene expression is tightly coupled to envelope gene expression through the IRES sequence.

The MLV retrovirus component is flanked by the Ad5 ITRs and packaging signal. As the MLV component is about 9.7 kb in size (8.5 kb MLV genome+0.5 kb IRES+0.7 kb GFP transgene), the adenovirus ITRs and packaging signal sequences combined are about 1.5 kb in size, and the pUC plasmid backbone is about 2.3 kb in size, the total size of the hybrid vector construct is therefore approximately 13.5 kb. Although this size is well below the minimal packaging size limit for adenovirus, is has recently been shown that smaller genomes can be packaged through the formation of multimers or concatemers, so long as multimers of the genome are within the 27 to 38 kb packaging size constraints of the adenovirus (Parks and Graham, 1997).

Example 3

Expression of Hybrid Vector Constructs in 293 Cells with Helper Adenovirus Complementation This example shows that hybrid vectors containing replication competent retroviral regions can be expressed to produce retroviral particles in cultured cells.

The retrovirus-adenovirus hybrid construct pRAd-g1ZDGFP was co-transfected into $2\times10_6$293 cells along with a helper adenovirus genome, Ad-hprt (Mitani et al., 1995), a standard E1-deleted adenovirus vector containing the hypoxanthine phosphoribosyltransferase gene, by calcium phosphate precipitation. The 293 cells were overlayed with agar,,and incubated until plaque formation was observed, about 5 days later (see also FIG. 8, below). Cell lysate from a total of 100 plaques was collected and individually re-inoculated on fresh 293 cells in 96-well plates. After incubation for 48 to 72 hours, until the cells spontaneously detached from the wells due to cytopathic effect of the adenovirus, the culture was harvested and any remaining intact cells were lysed by 3 freeze-thaw cycles. After spinning down cell debris, the virus-containing. supernatant was used to further amplify each virus isolate by individually reinoculating fresh 293 cells in 24-well plates. The amplification procedure was repeated until adequate stocks of adenovirus were obtained for each plaque originally isolated.

As the RAd-g1ZDGFP hybrid construct contains the GFP marker gene as part of the retrovirus component, it is possible to detect the presence of this sequence by UV fluorescence microscopy or by flow cytometry. Assuming that a majority of the plaques isolated would represent Ad-hprt helper virus alone, and that even in plaque isolates containing the helper-dependent hybrid construct there would be a very low initial titer which would at first be difficult to detect by flow cytometry, we initially screened for the presence of the hybrid construct by directly examining the 293 cells used for amplification of the adenovirus stocks by UV fluorescence microscopy.

Figure 9:
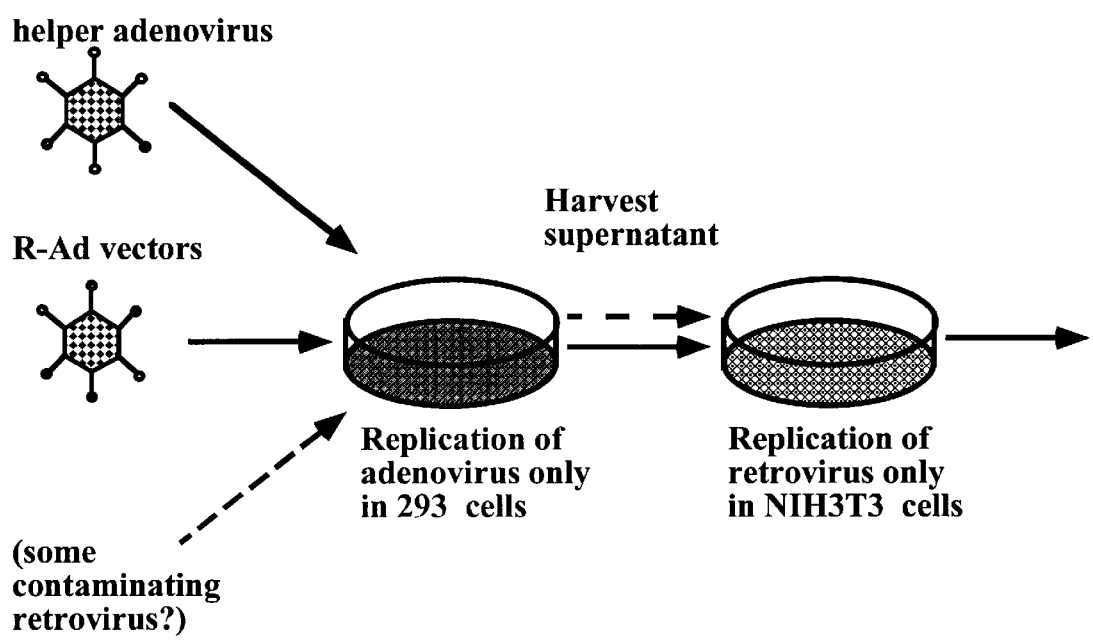
FIG. 9 illustrates an assay for transduction by retrovirus-adenovirus hybrid vectors.

We have been able to detect the presence of occasional fluorescent cells in some samples of 293 cells infected with the original plaque isolates, and this was confirmed by the presence of larger numbers of fluorescent cells in the same candidates after further rounds of amplification. In some cases the preliminary observation of fluorescent cells in the 293 cells inoculated with the original plaque isolate material could not be subsequently confirmed. We interpreted this as either carryover of 293 cells or cellular debris from the initial transfection when the plaques were being picked, or as unstable isolates of the helper-dependent adenovirus. Another event which is predicted to occur is the production of MLV retrovirus directly from the plasmid used to transfect 293 cells. This may initially be present as a contaminant in the plaque isolate material; however, as the 293 cells are of human origin, the serial amplification process should result prevent further propagation of such a contaminant, as the ecotropic strain of MLV retrovirus is incapable of binding to and infecting human cells (Weiss et al., 1984; Yoshimoto et al., 1993). On the other hand, 293 cells newly transduced via the adenovirus carrier vector will also transcribe the retrovirus component and transiently produce de novo retrovirus vectors, which can be harvested from the supernatant. Alternatively, these retroviruses can be removed by adequate washing of the cells, prior to harvesting of intracellular adenovirus (see also FIG. 9, below). Both retrovirus and adenovirus produced by the 293 cells can be harvested and used for subsequent NIH3T3 cell infection experiments.

Example 4

Serial Passage Through NIH3T3 Cells Shows Propagation of Retrovirus Vector Component The cell culture supernatant is harvested from 293 cells in which individual isolates of adenovirus were being amplified, usually about 48 to 72 hours after inoculation, when cytopathic effects can be observed but prior to complete cell lysis. Thus at this time point, retrovirus expressed from the helper-dependent adenovirus should be constitutively budding off into the supernatant, which can be harvested, filtered, and used to infect NIH3T3 cells. On the other hand, most of the replicating adenovirus should still be contained intracellularly and little adenovirus should be present in the cell culture supernatant. Therefore adenovirus can also be harvested by carefully washing the 293 cells after the cell culture medium is removed, collecting the cells by scraping them off the plate, lysing by 3 freeze-thaw cycles, and centrifuging to pellet the cell debris. Transduction of NIH3T3 cells by both 293 cell culture supernatant preparations and 293 cell lysate preparations can be confirmed by UV fluorescence microscopy to detect GFP expression. The supernatant from the first round of NIH3T3 transduction can also be harvested, filtered, and used to infect a fresh plate of NIH3T3 cells, and again transduction can be confirmed over serial passages by UV light microscopy or flow cytometry (assay illustrated in FIGS. 4 and 5). As human adenoviruses can enter and transduce murine cells such as NIH3T3 but are normally incapable of multiplying within them due to post-entry intracellular blocks to viral replication (Lucher, 1995), and especially as the helper adenovirus is E1-deleted and in any case requires trans-complementation of E1 in order to replicate, any adenovirus contaminant that might be present within the harvested 293 cell culture supernatant should be eliminated by serial passage in NIH3T3 cells (see also FIG. 9, below). Conversely, the MLV retrovirus readily propagates within the NIH3T3 cell culture, and this provides evidence for the production of true retrovirus vectors from the adenovirus carrier.

Structural analysis of the retroviral genome also provides evidence for retroviral vector production. This assay is illustrated in FIG. 6. Genomic DNA isolated from $10_6$ NIH3T3 cells was obtained over 7 serial passages, digested with Nhe I (which cuts only twice within the g1ZDGFP sequence, i.e., once within each LTR) to release almost the entire retroviral genome, and analyzed by Southern blot using a probe hybridizing to the GFP transgene sequence. A plasmid containing the g1ZDGFP genome was used as a positive control. Genomic DNA from NIH3T3 cells infected with wild type MLV retrovirus was used as a negative control. The serial passages are denoted as infection numbers 1 through 7.

Example 5

Construction and Production of Replication Defective Retrovirus-adenovirus Hybrid Vectors In addition to replication-competent retroviral vectors as secondary vector elements, retrovirus-adenovirus hybrid constructs containing a replication-defective retroviral vector packaging system are described. Such a packaging system requires a packaging-defective ($\Psi^-$) retrovirus structural gene cassette (gag, pol, env) and a packageable ($\Psi^+$) vector construct, both contained between the adenoviral ITRs. As it would appear to be advantageous to minimize the number of repeat sequences present in the hybrid vectors in order to maintain plasmid stability, when constructing the replication-defective retrovirus-adenovirus hybrid vector we delete or replace the retroviral LTR sequences wherever possible.

Specifically, the 5' MLV LTR that normally drives transcription of the gag, pol, and env genes is deleted and replaced with the SV40 early promoter/enhancer, and the 3' MLV LTR is replaced with SV40 splice and polyadenylation signals. Thus repeat sequences can be completely eliminated from the retroviral structural gene cassette. Next, repeat sequences are minimized in the LTRs of the $\Psi^+$ retroviral vector construct by the use of a hybrid CMV-LTR promoter, a strategy that has been previously employed with both MLV and HIV LTRs (Cannon et al., 1996; Soneoka et al., 1995). We exactly position the CMV promoter so that the transcriptional start site is the same as that directed by the natural MLV U3 promoter. The hybrid CMV-MLV R promoter unit created not only reduces the amount of sequence homology between the 5' and 3' LTRs, but also has the additional advantage of driving high level transcription in 293 cells, in which the native MLV LTR does not function as a particularly strong promoter. Another elegant feature of this system is that, because the CMV transcriptional start site is synchronized with that of the natural MLV start site, no CMV promoter sequences are introduced into the viral RNA genome; thus, after entry into the host cell and reverse transcription to produce the double-stranded DNA provirus which will subsequently integrate into the host cell genome, this hybrid LTR vector design results in complete reconstitution of the original MLV LTR. In this example, the vector itself contains the neomycin-resistance (neo$^R$) and GFP marker genes, but of course other genes of interest may be substituted.

Figure 7:
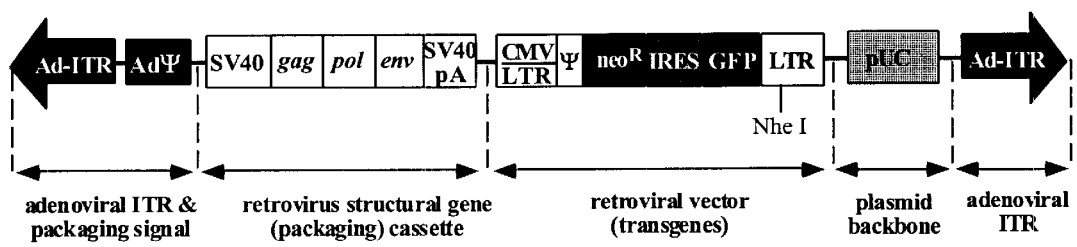
FIG. 7 shows the retrovirus-adenovirus hybrid vector construct RAd-SGPE/CNG.

This retroviral packaging/vector system is therefore at least 12 kb in size (at least 9 kb SV40 driven-structural gene cassette+at least 3 kb CMV/LTR driven neo$^R$/GFP transgene vector) and thus could not be contained within a standard adenovirus vector, which usually has a maximum capacity of 7 to 8 kb at best. Therefore we again use the helper-dependent adenovirus system as a first-stage carrier for this complete retroviral packaging/vector system, by flanking the retroviral components with the adenoviral ITRs and adenovirus packaging signal. The second-stage retrovirus produced after adenovirus vector transduction is therefore a replication-defective retroviral vector packaging the neo$^R$ and GFP transgenes. This construct design is shown in FIG. 7.

Figure 8:
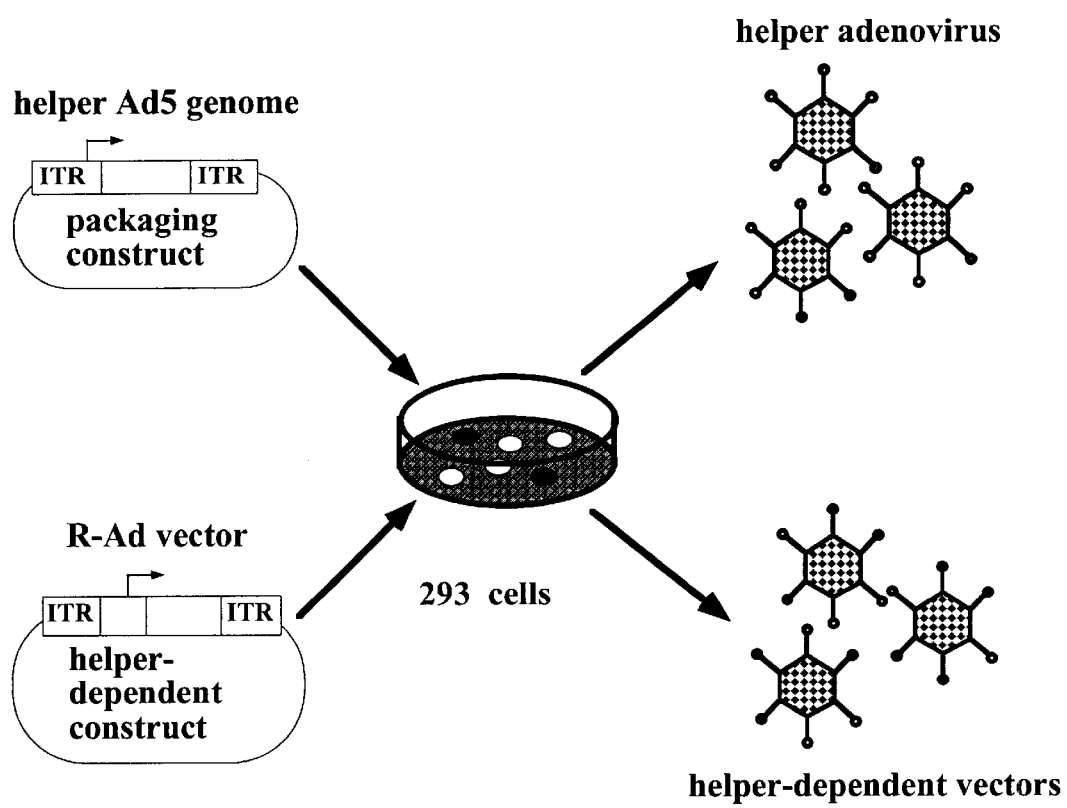
FIG. 8 illustrates the production of helper-dependent adenovirus.

The functional integrity of the retroviral packaging system can first be tested by direct transfection of the RAd-SGPE/CNG plasmid DNA into 293 cells, and determination of resultant retroviral titers on NIH3T3 cells. If, as expected, the construct is found to be capable of producing replication-defective retrovirus vectors, the retrovirus-adenovirus hybrid construct pRAd-SGPE/CNG is then co-transfected into $2 \times 10^6$ $^{293}$ cells along with the helper adenovirus genome Ad-hprt by calcium phosphate precipitation. The 293 cells are overlayed with agar and incubated until plaque formation is observed, about 5 days later. Cell lysate from a total of 100 plaques is collected and individually re-inoculated on fresh 293 cells in 96-well plates (FIG. 8). After incubation for 48 to 72 hours, when cytopathic effects of the adenovirus are observed to cause cell detachment and lysis, the entire culture is harvested and any remaining intact cells lysed by 3 freeze-thaw cycles, and centrifuged to remove cell debris. The viral supernatant thus obtained is used to further amplify each virus isolate by individually re-inoculating fresh 293 cells in 24-well plates. The amplification procedure is repeated using progressively larger plates until adequate stocks of adenovirus are obtained for each plaque originally isolated.

As described above, retroviruses are produced from individual isolates of adenovirus amplified in 293 cells that are harvested by collection of the supernatant cell culture medium about 48 to 72 hours after inoculation, when cytopathic effects can be observed but prior to complete cell lysis. The collected medium is filtered through a 0.45 $\mu$m syringe filter to remove cell debris, and used for NIH3T3 cell infection experiments. In addition, as adenoviral replication should be proceeding and adenovirus particles accumulating intracellularly at this time point, the 293 cells are also harvested to obtain adenovirus preparations. Thus, as previously, after collecting the retroviral supernatant and careful washing to remove residual retrovirus, the adenovirus produced in the 293 cells is harvested by scraping the cells from the plate, followed by 3 freeze-thaw cycles to lyse the cells, and centrifugation to remove cell debris.

Using the replication-defective retrovirus-adenovirus vector, multiple rounds of serial propagation of the retrovirus vector will not occur. In fact, there should be no propagation at all of the replication-defective retrovirus preparations directly harvested from 293 cells. On the other hand, the initial transduction event in NIH3T3 cells infected by adenovirus harvested from the 293 cell lysate, should then give rise to a single round of replication-defective retrovirus production, which can in turn be harvested from the NIH3T3 cell supernatant and used for a second round of NIH3T3 infection. As the adenovirus carrier does not replicate in NIH3T3 cells, thus any adenoviral contaminants that might potentially be carried over in the second round of NIH3T3 infection should be eliminated through adequate washing of the NIH3T3 cells 6–12 hours prior to harvesting retrovirus from the supernatant. No further propagation of the replication-defective retrovirus vector should occur after the second round of NIH3T3 infection.

Additionally, the multiplicity of infection (MOI) of the initial adenovirus transduction can be titrated down to 0.01 or 0.001 relative to the number of NIH3T3 cells plated, in which case the percentage of GFP-positive cells should gradually increase over a period of several days in culture due to continued expression of the retrovirus vector from the adenovirus carrier, as long as adenovirus expression persists in the initially transduced cells.

Figure 10:
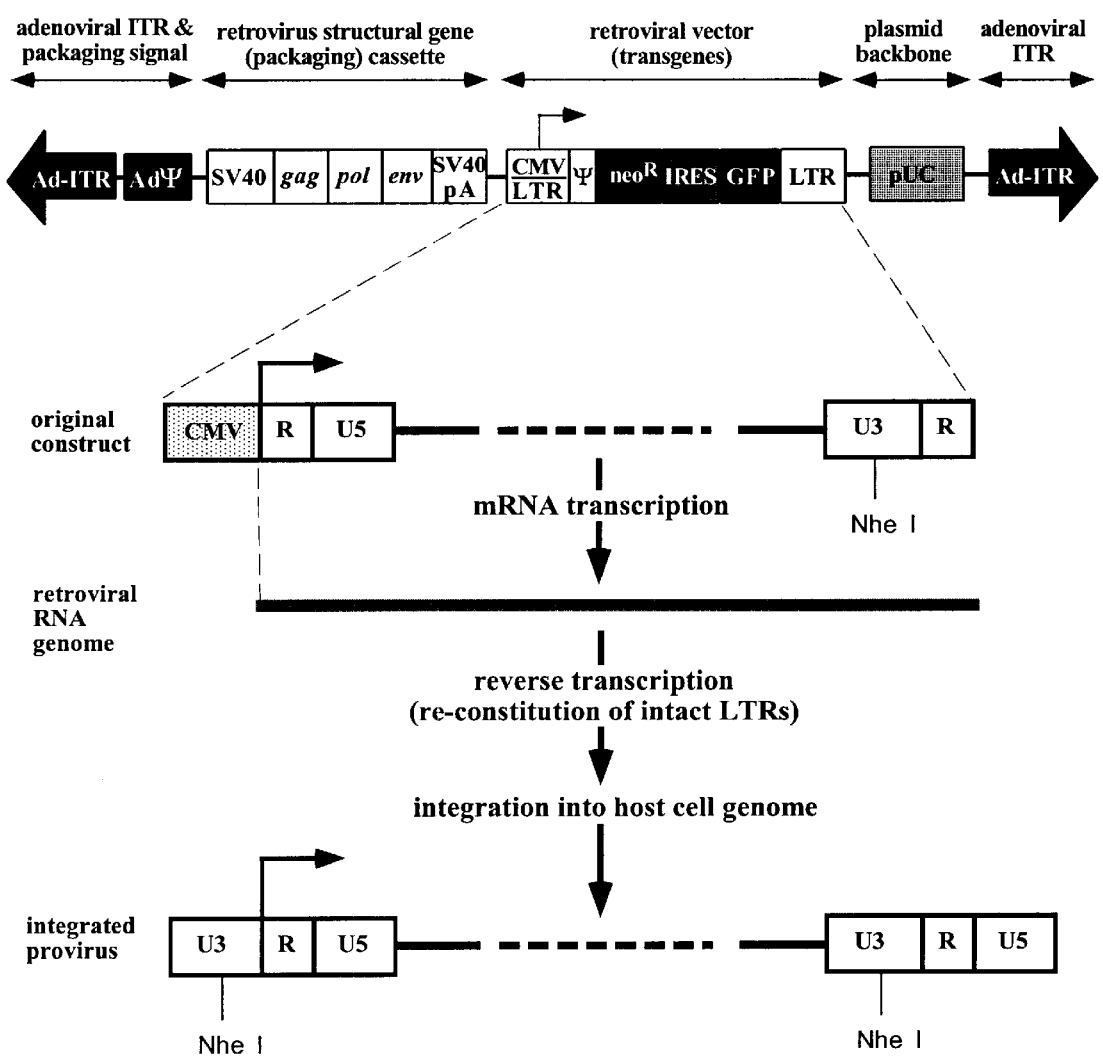
FIG. 10 shows a Southern blot assay for detection of properly reverse transcribed retroviral DNA.

As previously described, the GFP-positive cells can be visualized by UV fluorescence microscopy, and quantitated by FACS analysis. Furthermore, genomic DNA can be isolated from the transduced NIH3T3 cells (both first-round and second-round transductions) and analyzed by Southern blot using probes against the retrovirus vector transgene sequences, to confirm stable integration of the transgenes after retroviral transduction. In order to distinguish between retroviral vector sequences derived from properly reverse transcribed and integrated retrovirus versus the original retroviral sequences present in the adenoviral DNA (which may persist as an episome and therefore contaminate the genomic DNA preparation), the Southern blots are prepared by restriction digest of genomic DNA with Nhe I, which cuts once within each intact retroviral LTR. Thus, properly reverse-transcribed proviral sequence should re-duplicate both LTRs, resulting in release of the integrated full-length retroviral vector fragment of predicted size upon Nhe I digest (FIG. 10). Conversely, the original retroviral vector construct contained within the adenovirus DNA has non-identical ends (i.e. U3-deleted CMV-MLV 5' LTR and U5-truncated 3' LTR, see FIG. 10), and the Nhe I site in the 5' LTR is eliminated due to substitution with CMV sequences; thus only one Nhe I site will be present, in the 3' LTR, and retrovirus vector-specific probe hybridization of Nhe I-digested adenoviral DNA shows a different band size. In addition, the presence of the neomycin resistance gene as a marker enables us to select the transduced NIH3T3 cells in G418 to functionally test for stable long-term transduction.

Example 6

Construction and Production of Retrotransposon-adenovirus Hybrid Vectors

We also describe the process of constructing retrotransposon-adenovirus hybrid vectors. Our collaborators, Dr. H. Kazazian and Dr. J. Moran (U. Penn), have generously provided us with an L1 retrotransposon element/reporter gene construct that has been described above ((Moran et al., 1996), see Background). This element, L1.3, has the highest retrotransposition frequency of all the human LINEs tested, and the reporter gene cassette is inserted into its 3' untranslated region in the reverse (antisense) orientation. The reporter cassette consists of the $neo^R$ gene, which is disrupted by an intron (IVS 2 of the g-globin gene) in the opposite transcriptional orientation with respect to the $neo^R$ gene (i.e., intron is in the sense orientation with respect to the overall L1 construct), and is flanked by SV40 promoter and polyA sequences (see FIG. 11). This arrangement ensures that G418 resistance will only arise if the L1 retroelement is transcribed from its 5' promoter, the mRNA is spliced to remove the intron disrupting the $neo^R$ coding sequence, the element is then reverse transcribed and re-integrated into chromosomal DNA, and now intact $neo^R$ gene is expressed from the SV40 promoter in the antisense direction. Thus only actual retrotransposition events will be scored. In contrast, transcripts originating directly from the SV40 promoter cannot be spliced, an intact $neo^R$ gene product cannot be produced, and the cells will not become G418 resistant and therefore will not be scored in this assay.

Figure 11:
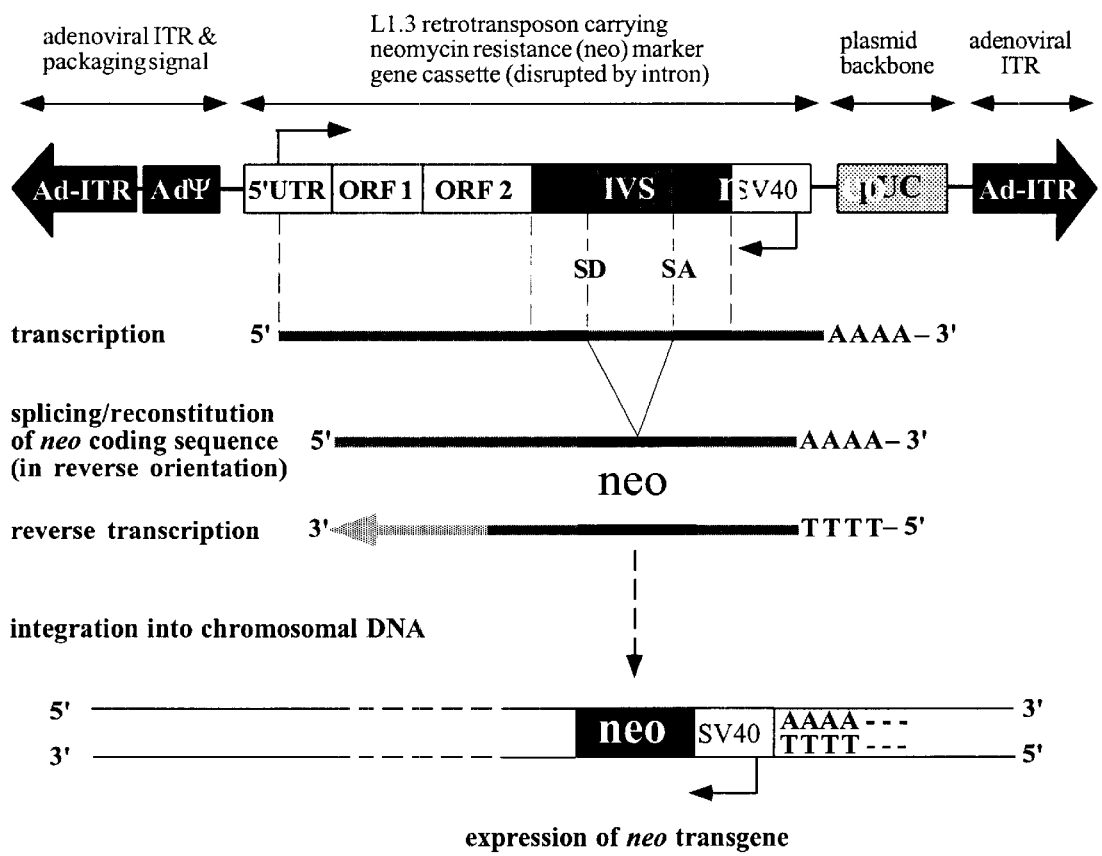
FIG. 11 illustrates the retrotransposon-adenovirus hybrid vector construct RAd-L1.3 neo.

This L1 retrotransposon/reporter cassette system is approximately 8.1 kb in size (6 kb L1.3 retrotransposon sequence+2.1 kb $neo^R$ reporter gene cassette). In order to use the helper-dependent adenovirus system as a first-stage carrier for this retrotransposon vector, we add flanking adenoviral ITRs and the adenovirus packaging signal to the L1 construct. The second-stage retrotransposon produced after adenovirus vector transduction therefore mediates proper splicing, reverse transcription, and stable integration of the $neo^R$ transgene. This construct design is shown in FIG. 11.

As previously described, the retrotransposon-adenovirus hybrid construct pRAd-L1.3neo is co-transfected into $2 \times 10^6$ 293 cells along with the helper adenovirus genome Ad-hprt by calcium phosphate precipitation. The 293 cells are overlayed with agar, and incubated until plaque formation is observed, about 5 days later. Cell lysate from a total of 100 plaques is collected and individually re-inoculated on fresh 293 cells in 96-well plates. After incubation for 48 to 72 hours, these cells are detached from the wells using a non-enzymatic buffer containing 2 mM EDTA in phosphate-buffered saline, lysed by 3 freeze-thaw cycles, and after spinning down cell debris, the supernatant is used to further amplify each virus isolate by individually reinoculating fresh 293 cells in 24-well plates. The amplification procedure is repeated using progressively larger plates until adequate stocks of adenovirus are obtained for each plaque originally isolated.

Testing Transduction Efficiency and Stable Integration of the Transgene in Cell Culture About 48 to 72 hours after inoculation, when cytopathic effects can be observed but prior to complete cell lysis, the 293 cells in which individual isolates of adenovirus are being amplified are harvested by repeated freeze-thaw cycles to lyse the cells. The cell debris is pelleted, and the supernatant is used as the crude virus preparation for subsequent NIH3T3 infection. Although the retrotransposon component of the hybrid vector presumably will integrate the properly spliced $neo^R$ transgene into the genome of the 293 cells used for amplification, the presence of the helper virus will cause cytopathic effects and result in cell death of clones even if they are G418 resistant. Again, as adenovirus does not replicate in NIH3T3 cells, it should therefore be possible to test for retrotransposition and transgene expression by G418 selection in NIH3T3 cells. Furthermore, genomic DNA can be isolated from the transduced NIH3T3 cells and analyzed by Southern blot using probes against the retrovirus vector transgene sequences, in order to confirm stable integration of the transgenes. The $neo^R$ transgene must be properly spliced in order to remove the disrupting intron sequence, and so any G418 resistant cells should be derived from authentic retrotransposition events. This can be confirmed by the size of the transgene sequence detected on Southern blots, and by PCR using neomycin sequence primers that span the intron insertion site.

Example 7

Testing the Transduction Efficiency and Duration of Transgene Expression in the Liver by Tail Vein Injection of R-Ad Vectors in C57bl/6 Mice Hybrid retrovirus-adenovirus or retrotransposon-adenovirus vectors are tested for their ability to mediate efficient and stable transduction in vivo, and for their immunogenicity, using an immunocompetent C57bl/6 mouse model. In vitro systems using pure populations of cultured cell monolayers are inadequate to address issues relating to the efficiency of gene delivery in, the context of the mixed quiescent and proliferating cell populations present in vivo and the architectural complexity of intact tissues. Furthermore, other parameters such as the optimal route and method of delivery, dose response and optimal titer, safety or toxicity of high dose virus preparations, duration of expression in transduced cells in situ, and the possibility of an immune response, can only be investigated in vivo.

Each hybrid vector preparation is harvested from 10 inoculations of 293 cells in T175 flasks, which normally produce a titer of $10^{9-10}$ per ml per flask. The cells are lysed by 3 cycles of freeze-thawing, the cell debris pelleted, and the helper-dependent virus purified by cesium chloride gradient centrifugation. The animals are first anesthetized with an inhalational general anesthetic such as halothane or metaphane, and the induction of an adequate level of anesthesia confirmed by areflexivity to stimuli such as tail pinch. Control infections using GFP-negative vectors are performed in parallel. In addition, standard E1-deleted first generation adenovirus, vectors carrying the GFP marker gene are used as a "positive" control series for each experiment. Virus preparations are injected by tail-vein injection and assayed for transduction in the liver.

Four days, fourteen days, and twenty-one days after administration of the virus preparations, transduction efficiency and immune response against the vectors is assessed. At this point, the animals are humanely sacrificed by an overdose of inhalational anesthetic followed by cervical dislocation, in accordance with the recommendations of the Panel on Euthanasia of the American Veterinary Medical Association. Tissues are then harvested, including liver specimens for fixation, staining and histological examination, and splenocytes collected for CTL assays (see below). Tissue samples are snap frozen in liquid nitrogen and frozen sections cut on a cryostat, mounted on polylysine-coated glass slides, and examined by UV fluorescence microscopy for GFP expression. Sections are also fixed with 4% paraformaldehyde and 0.1% glutaraldehyde in PBS (pH 7.4), and stained with hematoxylin-eosin for histological examination to assess whether any inflammatory infiltrate is present. The efficiency and immunogenicity of the hybrid vectors is assessed by comparison with samples from the negative and positive control adenovirus experiments. Some tissue samples can also be lysed for genomic DNA extraction, and transgene integration assayed by Southern blot.

Example 8

A Cre-lox System for Helper-dependent Virus Production

During the process of expanding plaque isolates of RAd-g1ZDGFP in progressively larger scale cultures for further experiments, we encountered technical difficulties in the amplification process, as growth of the helper-dependent form is quite poor compared to the helper virus. Therefore, a new system for amplification of helper-dependent viruses, using 293 -cre cells, has been established, using reagents obtained from Merck. Similar helper adenovirus systems are described in, for example, Ng. P. et al. (1999) A high-efficiency Cre/loxP-based system for construction of adenoviral vectors. Hum. Gene Ther. 10:2667–72.

Figure 12:
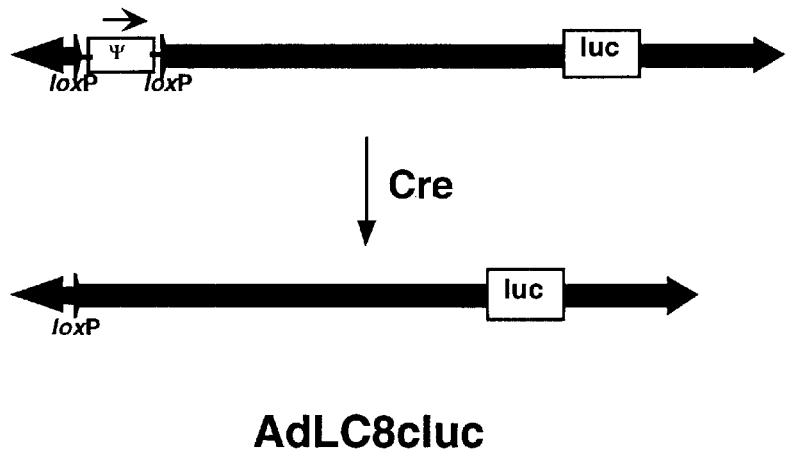
FIG. 12 illustrates recombination of loxP site-containing helper adenovirus vectors in Cre recombinase expressing cell lines. The packaging signal (ψ)of the helper adenovirus AdLC8cluc is flanked by loxP sites. Upon introduction into 293Cre4 cells, the Cre recombinase removes the packaging signal, thus inhibiting the ability of the helper adenovirus to propagate.

This system confers a growth advantage to the helper-dependent form by using a crippled helper virus which has loxP sites flanking the viral packaging signal (AdLC8cluc). Thus, when grown in 293-derived cell line expressing the Cre recombinase (293Cre4), the helper virus will provide essential viral functions in trans, but its own packaging signal will be efficiently deleted, resulting in more efficient packaging of the helper-dependent construct (FIG. 12). The packaging signal of the helper virus was found to be excised at an efficiency of 80–100% in the 293Cre4 cells.

For propagating a helper-dependent vector, AdSTKCMVb, we transfected 293Cre4 cells in 60-mm dishes with pSTK120CMVb DNA, which contains the lacZ reporter gene. Twenty-four hours after transfection, the cells were infected with AdLC8cluc, which contains the luciferase reporter gene, and harvested 72 hr after infection. Viruses were released by freezing and thawing and used for a next round of amplification. At each round of amplification with increasing scale, 293Cre4 cells were infected with an aliquot of AdSTKCMVb and with AdLC8cluc at an MOI of 1.

Figure 13:
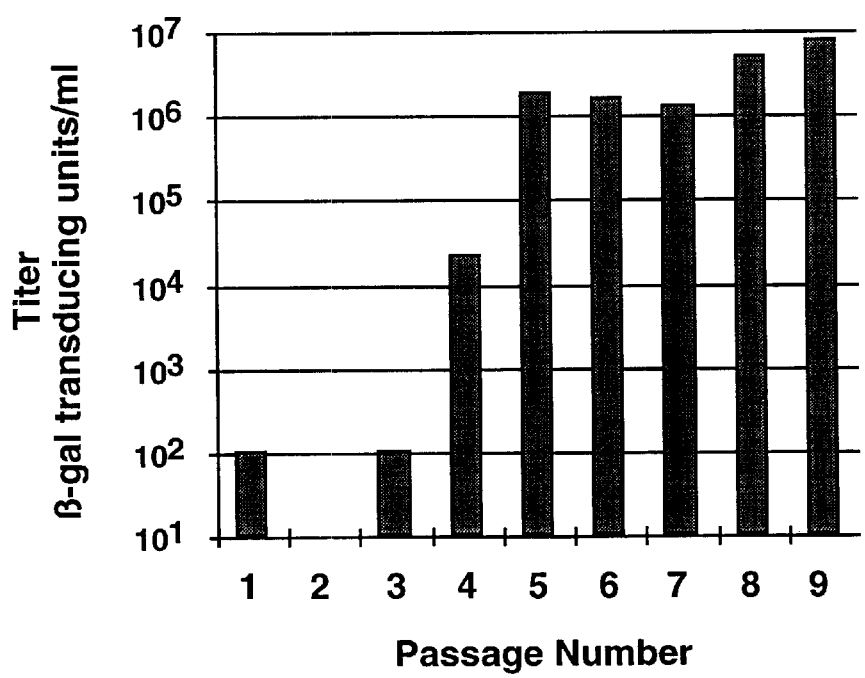
FIG. 13 demonstrates the improved growth of helper-dependent vector using the Cre-lox system. The helper-dependent adenovirus vector AdSTKCMVb was grown with the helper adenovirus AlC8cluc in the 293Cre4 cell system. The bar graph shoes the titer of the helper-dependent vector over serial passages. The titer is initially quite low, but eventually reaches $10^{6-7}$ per ml using the Cre-lox system.

During propagation, the titer of AdSTKCMVb was monitored (FIG. 13) by infecting A549 cells with the diluted vector followed by the X-gal staining. The titer was $7.6 \times 10^6$ after 9 rounds of amplification. The structure of the vector was also confirmed by Southern hybridization, and no deletion was found.

Example 9

The Retrovirus-adenovirus Hybrid Vector R-Ad 322

For propagating the helper-dependent retrovirus-adenovirus vector, R-Ad 322, we first constructed a plasmid containing the vector sequence, which is largely similar to RAd-g1ZDGFP. The hybrid vector plasmid pR-Ad 322 is based on pNEBITR2, which contains the adenoviral inverted terminal repeats (ITRs) with a 1 kb intervening stuffer sequence and the adenoviral packaging signal, a low copy number pBR322-based backbone, and contains the retroviral vector sequence for pCEemd, a replication-competent ecotropic retroviral vector that contains a hybrid 5° CMV/MLV LTR (to reduce 5' and 3' LTR homology, which is a cause of plasmid instability), the retroviral packaging signal, the retroviral packaging components gag, pol, and env, an IRES-driven enhanced GFP marker gene, and a 3' MLV LTR. As above, we transfected 293Cre4 cells in 60-mm dishes with pR-Ad 322 plasmid DNA, followed 24 hours later by infection with AdLC8cluc, and harvest at 72 hr after infection by freezing and thawing for the next round of amplification. At each round of amplification with increasing scale, 293Cre4 cells were infected with an aliquot of R-Ad 322 and with AdLC8cluc at an MOI of 1.

Figure 14A:
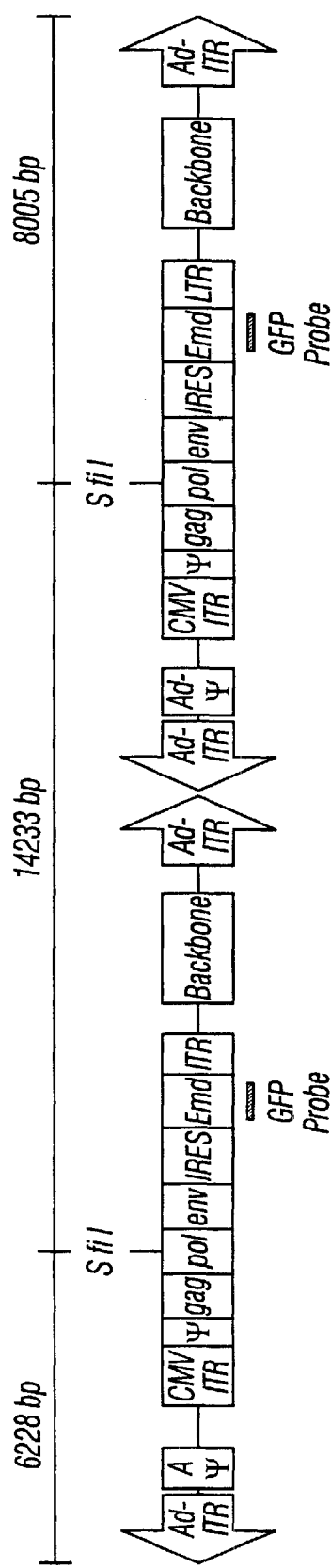
FIG. 14A shows a schematic representation of hybrid vector R-Ad322. Southern blot analysis shown in FIG. 14B shows that R-Ad322 Hirt prep DNA is a head to tail concatemer as indicated schematically in panel A. Lane 1 shows R-Ad322 Hirt prep DNA digested with Sfi I. Lane 2 shows R-Ad322 plasmid control DNA digested with Sfi I. The gel was probed with a random-primed probe against the green fluorescent protein (GFP) sequence of R-Ad322.
Figure 14B:
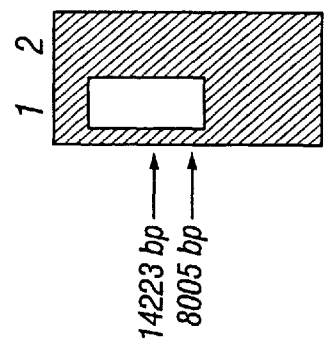

The genomic structure of the R-Ad 322 adenovirus was determined by Southern blot analysis of Hirt prep DNA to be a concatemer of two copies of the pR-Ad 322 sequence (FIG. 14). As shown in FIG. 14, when a digest of R-Ad 322 Hirt prep DNA using the restriction enzyme Sfi I was blotted and hybridized with a radiolabeled probe specific for the GFP sequence, a characteristic pattern of two bands of approximately 14 kb and 8 kb were observed, corresponding to the pattern that would be predicted to occur if the pR-Ad 322 sequences are linked in a head-to-tail configuration.

Example 10

The First Stage R-Ad 322 Adenovirus Can Infect Human Target Cells

Subsequently, the R-Ad 322 adenovirus preps were used for infection of HeLa human target cells, and GFP transgene expression was measured by FACS analysis of the infected population over several passages. As the pCEemd retrovirus component is derived from an ecotropic strain of MLV (i.e., its host range is restricted exclusively to murine species), any contaminating retrovirus component at this stage, even if present after surviving multiple freeze-thaws, would still be incapable of infecting human target cells.

Figure 15:
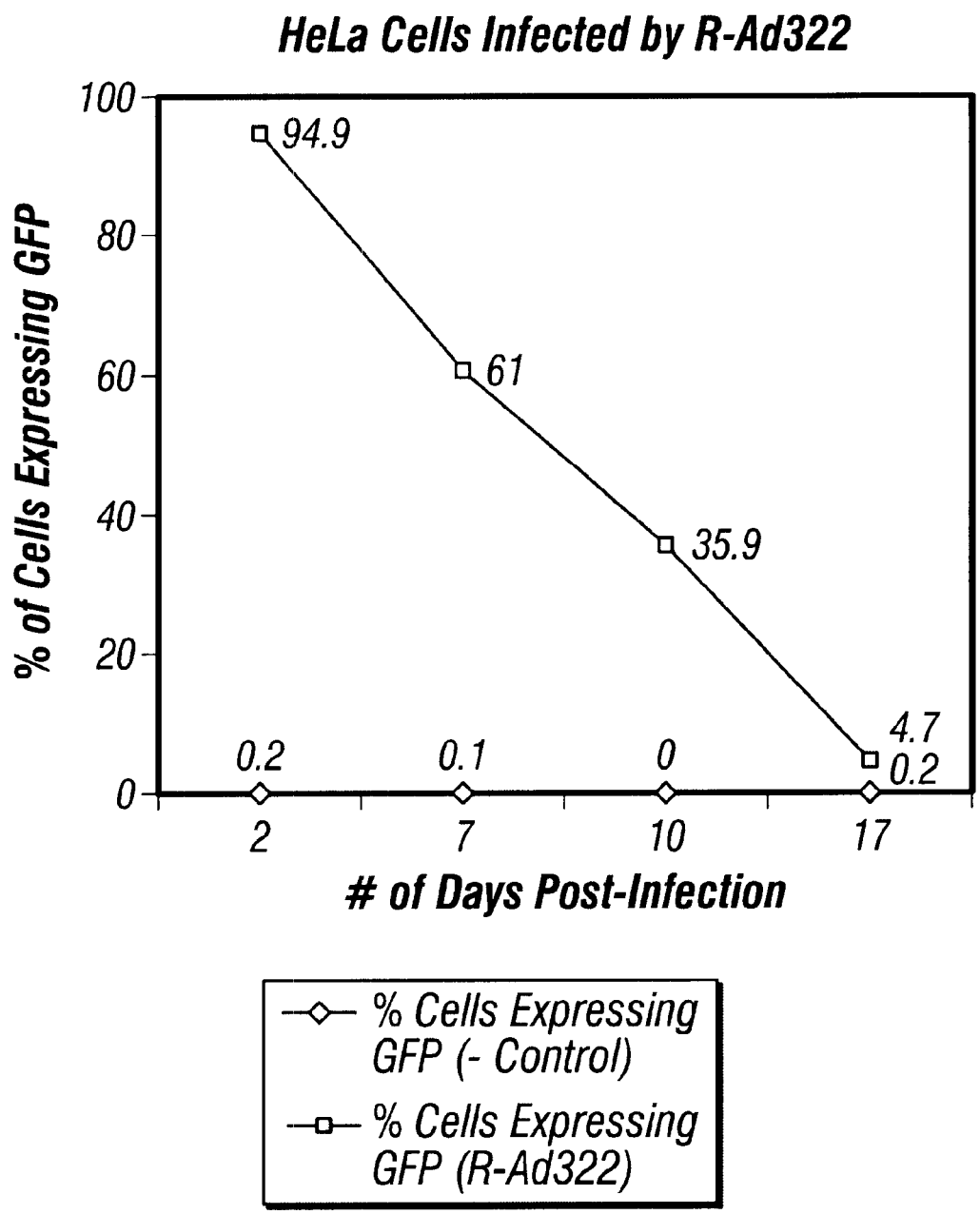
FIG. 15 demonstrates that R-Ad322 first-stage adenovirus can infect human target cells. The percentage of cells expressing green fluorescent protein (GFP) is graphed versus days after infection by the vector R-Ad322.

As shown in FIG. 15, the R-Ad first stage adenovirus is capable of efficient infection of the entire population of HeLa cells initially, after which the replication-defective adenovirus is gradually lost from the culture as the episome is diluted out of the population with progressive cell divisions. This latter point is also important, as it again indicates that the replication-competent ecotropic retrovirus component is not capable of infecting these HeLa cells, otherwise the GFP-positive population would have remained at its high initial level with stable integration of the retroviral component, and so this demonstrates that the adenovirus component is working independently of the retroviral component.

Example 11

Figure 16:
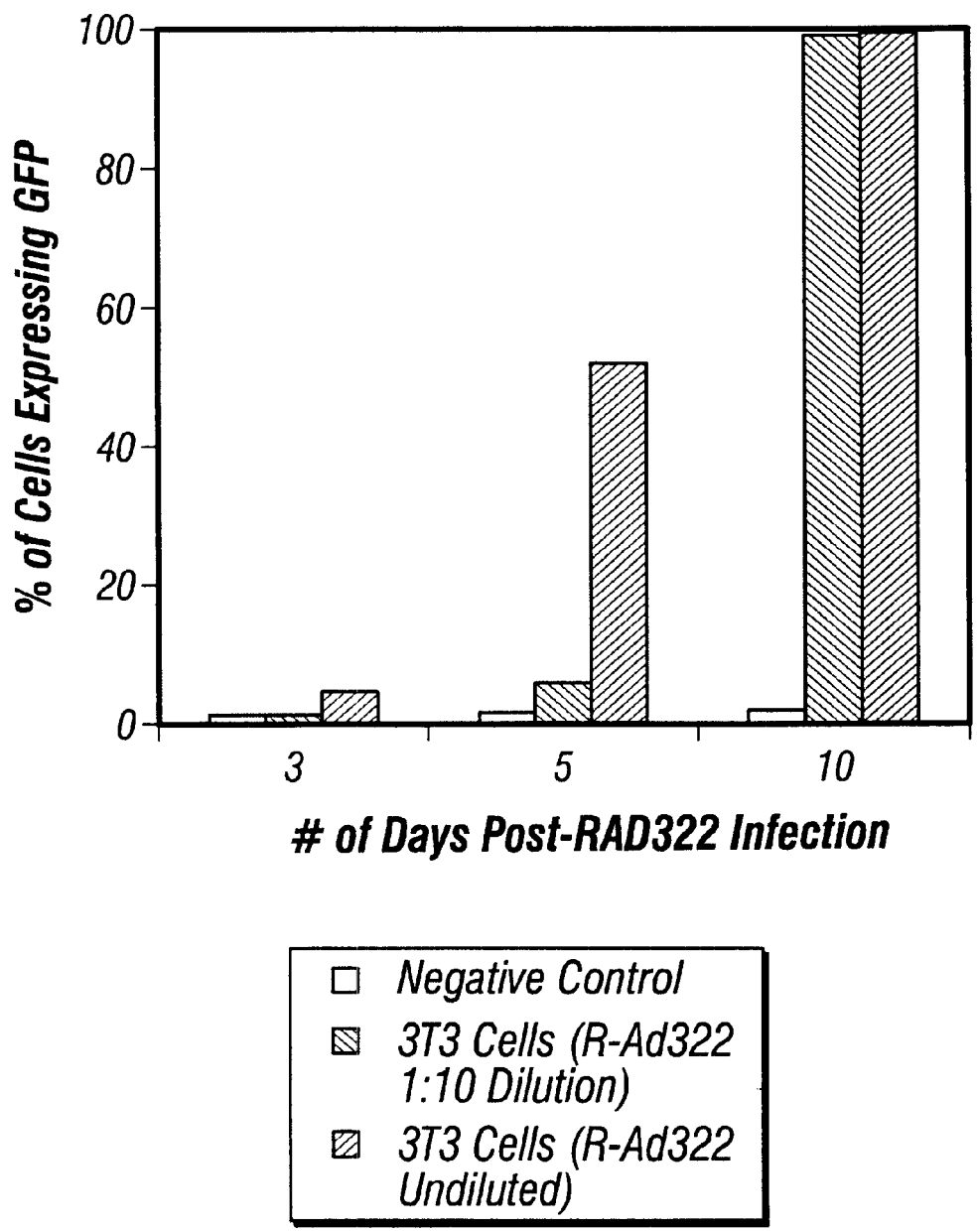
FIG. 16 shows that the R-Ad322 vector produces retroviral particles capable of infecting cultured human cells. NIH3T3 cells were infected with 293 cell culture supernatant containing R-Ad322 second-stage retroviral particles, at either the concentration of the supernatant or a 1:10 dilution, produced after infection of 293 cells by the first stage helper-dependent adenovirus vector. The percent of NIH3T3 cells expressing GFP is graphed versus days after infection.

The R-Ad 322 Hybrid Vector Results in Production of Second-stage Replication-competent Ecotropic Retrovirus Vectors that Can Infect and Propagate in Murine Target Cells The conditioned medium from HeLa cells infected with the R-Ad 322 adenovirus was harvested after serial washes and passage of the infected cells (to remove any retroviral vector that might have been carried over from the original infection prep), and used to infect murine NIH3T3 cells. GFP transgene expression was again measured by FACS analysis of the infected population over several passages. As shown in FIG. 16, progressive increase of cells expressing GFP was observed over time, confirming that the second stage retroviral vector was being produced by the infected HeLa cells and was budding into the conditioned medium, and was then capable of replicating and mediating spread of the GFP transgene throughout the NIH3T3 cell culture. As human adenoviruses are incapable of replicating in murine cells, and in any case as the helper-dependent adenovirus is incapable of replication outside of 293 cells even in the presence of the helper, this confirms that the second-stage retrovirus component is working independently of the adenoviral component.

In fact, progressive spread of the retrovirus component from a single adenovirus-infected HeLa cell seeded onto a culture of NIH3T3 cells could be visualized by UV fluorescence microscopy. Following the same field by light and UV fluorescence microscopy for after 1, 5 and 10 days showed that the retrovirus spread from a single adenovirus-infected HeLa cell to a multitude of cells.

Thus, we have definitively demonstrated a working hybrid vector system that consists of a first-stage helper-dependent adenovirus vector that is capable of infecting human cells with resultant transient production of a second-stage replication-competent ecotropic retrovirus that is capable of spreading in murine cells, resulting in enhancement of the original titer and permanent transduction.

Example 12

Construction of Retrotransposon-adenovirus Hybrid Vector pRAd-L1.3neo-GFP

Figure 17:
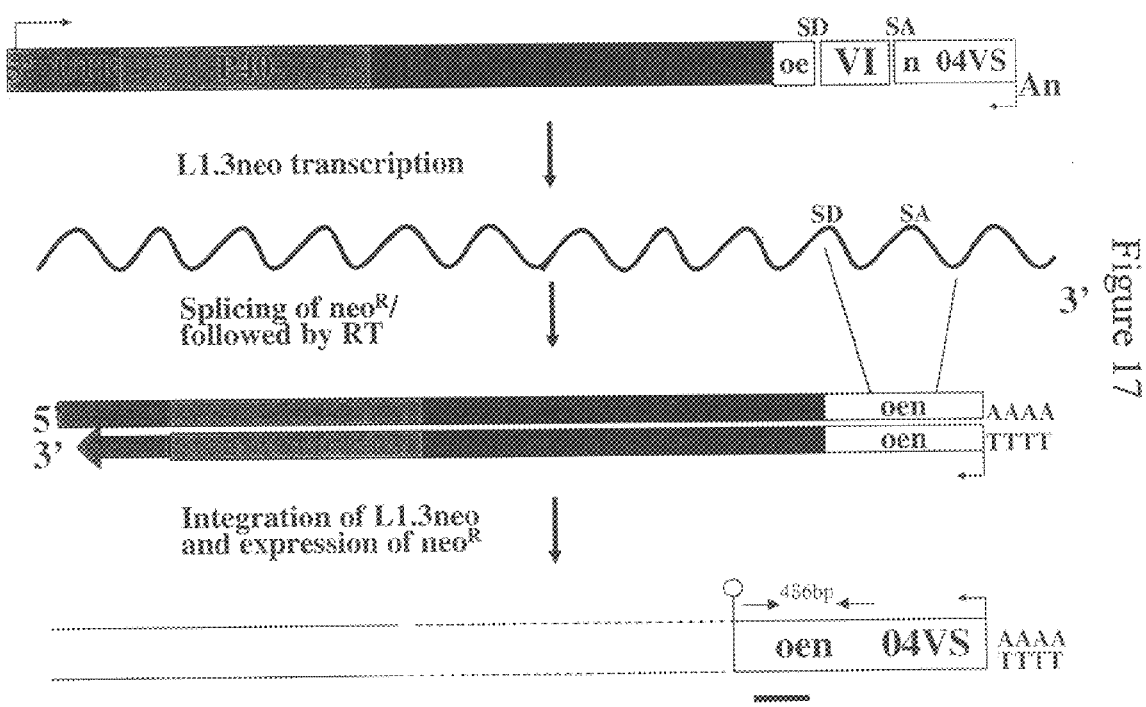
FIG. 17 schematically illustrates the assay used to score retrotransposition events. Successful retrotransposition involves splicing and integration resulting in the formation of a 486 bp reconstituted neomycin resistance gene (neo).

We have constructed a prototype retrotransposon-adenovirus hybrid vector, using an L1 retrotransposon element/reporter gene construct provided by our collaborators Dr. Haig Kazazian and John Moran. This L1 retrotransposon/reporter cassette system is approximately 8.1 kb in size (6 kb L1.3 retrotransposon sequence+2.1 kb SV40 promoter-driven neomycin resistance ($neo^R$) reporter gene cassette). The $neo^R$ cassette is in the reverse orientation from the retrotransposon, and its coding sequence is interrupted by a forward orientation intron sequence. This construct will thus result in stable integration and expression of a functional $neo^R$ gene and thus confer resistance to the antibiotic G418 only if correct retrotransposition occurs, by transcription of L1.3 mRNA, splicing of the RNA in the forward orientation, followed by reverse transcription of the spliced form and integration into genomic DNA so that the SV40 promoter can function to drive expression of the now intact $neo^R$ gene (FIG. 17). In order to use the helper-dependent adenovirus system as a first-stage carrier for this retrotransposon vector, we cloned the L1.3-neo cassette into the plasmid pSTK-GFP, which contains the adenoviral ITRs and packaging signal, along with a GFP marker gene driven by the CMV promoter and C346 cosmid stuffer sequence. The GFP marker is therefore outside the retrotransposon cassette but will still serve as a marker of adenoviral transduction. The resultant plasmid construct was designated HDL1.3 neo.

Figure 18:
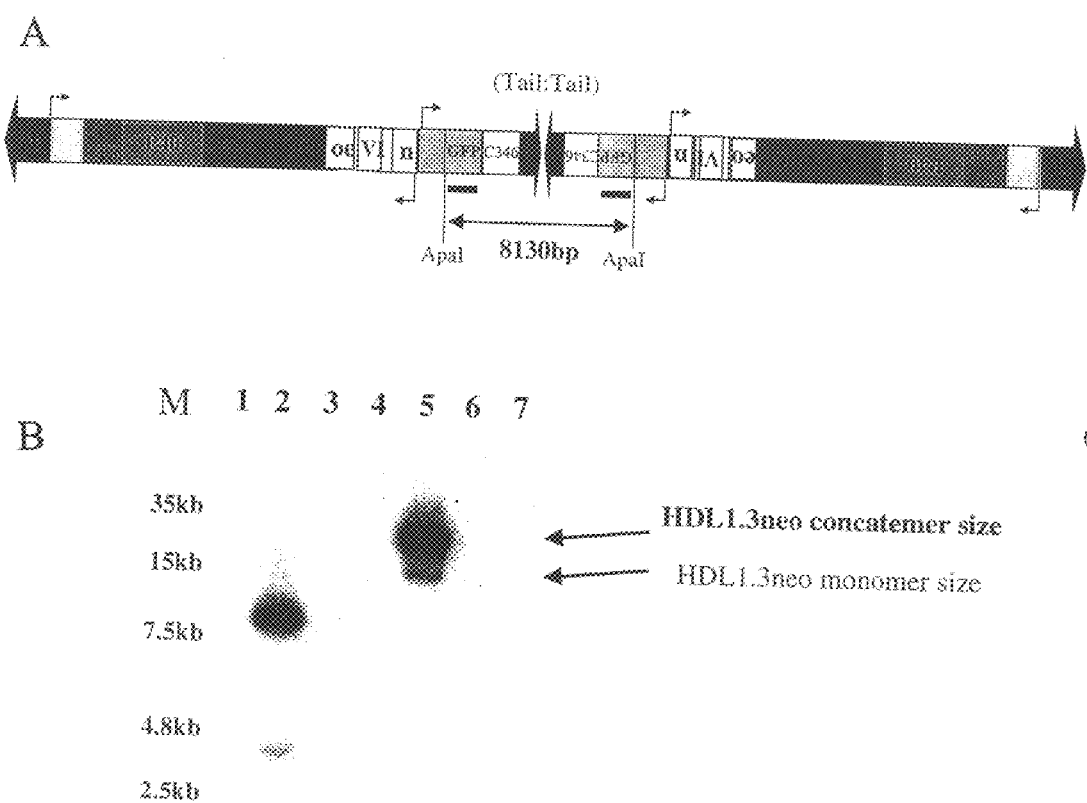
FIG. 18A shows a schematic view of hybrid vector HDL1.3neo.
FIG. 18B shows a Southern blot of crude HDL1.3neo DNA probed with GFP cDNA. The results indicate that HDL1.3neo is a mixture of concatemers.

After propagation of the HDL1.3 neo vector in the cre-lox system as above, Southern blot analysis of the adenoviral Hirt prep DNA was performed after Apa I digest using a GFP-specific probe to determine its genomic structure. As shown in FIG. 18, in this case the hybrid vector obtained appeared to predominantly consist of a tail-to-tail concatemer as evidenced by the presence of a characteristic 8 kb band, but an additional 4 kb band was also observed as a minor species, suggesting that a smaller population of head-to-tail concatemers might also be present, thus the HDL1.3 neo vectors obtained represent a mixed population. Interestingly, in addition to a band corresponding to the concatemerized length, a weaker signal corresponding to a monomer-size band was also present in undigested DNA samples, suggesting that in this case, vectors smaller than the previously reported 25 kb "minimal" adenovirus packaging size could also be packaged and propagated, and this could also account for the 4 kb band upon Apa I digest. Expression of the CMV-GFP marker cassette in the retrotransposon-adenovirus hybrid vector was confirmed by flow cytometric analysis of 293 cells and infected HeLa cells.

Example 13

Infection of HeLa Cells with Retrotransposon-adenovirus Hybrid Vector HDL1.3 neo The helper-dependent HDL1.3 neo adenovirus was used to infect HeLa cells, and 5 days after infection, the cells were subjected to selection with the neomycin analog G418. A dose-dependent increase in the number of G418-resistant colonies was observed with increasing concentrations of the HDL1.3 neo vector, confirming that the hybrid vector in the infected HeLa cells was mediating successful retrotransposition. A negative control showed no G418 resistant colonies. The retrotransposition frequency obtained in this experiment was calculated to be on the order of 1 in 2150 cells, but this was done with a multiplicity of infection (MOI) of less than 1 (i.e., the ratio of virus to cells was less than 1).

Figure 19:
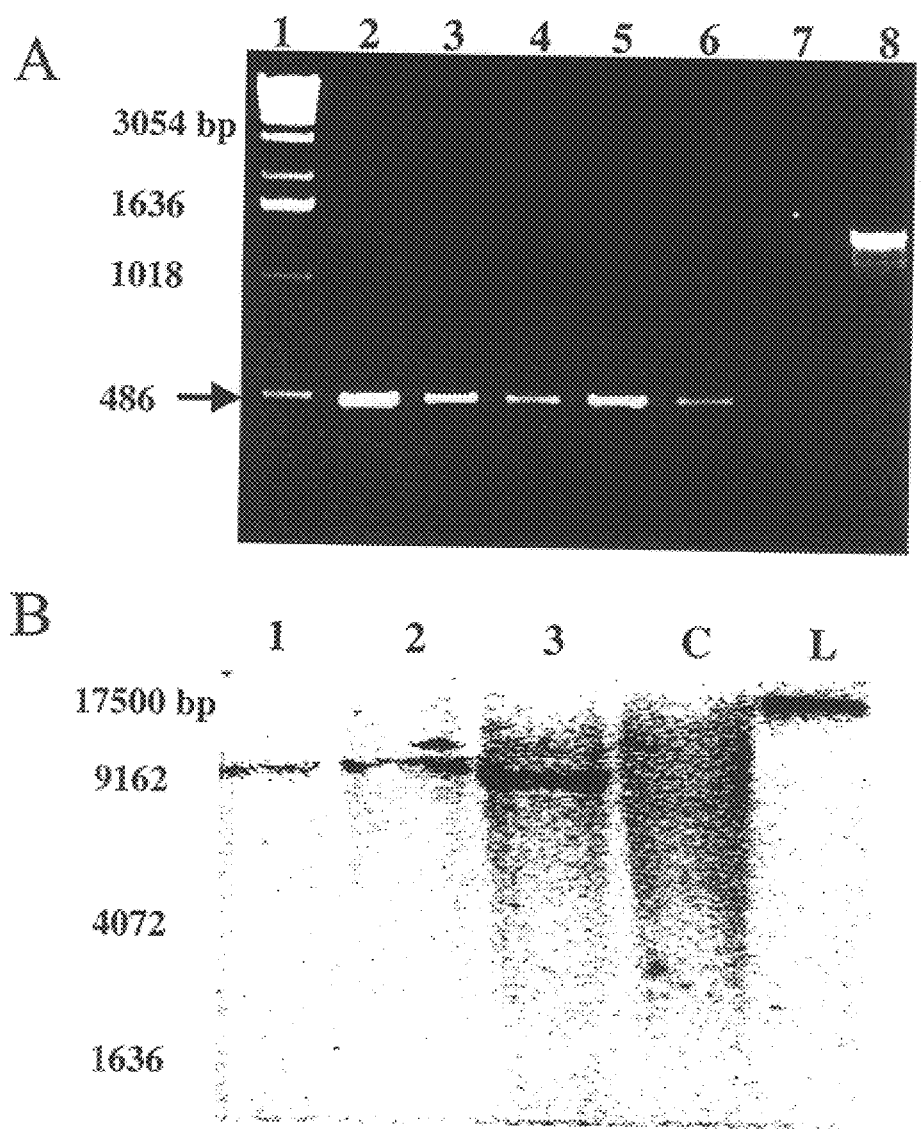
FIG. 19 (parts A–B) shows that the neoR transgene is successfully spliced and integrated in individual $G418_R$ clones that had been infected with the HDL1.3neo hybrid vector.

Both PCR and Southern blot analyses of individual colonies surviving G418 selection were performed (FIG. 19). Primers specific for the $neo^R$ gene, and situated at sites flanking the intronic sequence, were used to amplify genomic DNA from individual subclones.

The amplified band size corresponded to that of the spliced form, confirming that correct retrotransposition had occurred in these colonies. Furthermore, Southern blots probed with the $neo^R$ sequence showed that genomic integration of the retrotransposon component had indeed occurred.

Example 14

Increasing MOI Results in a Higher Retrotransposition Frequency

Figure 20:
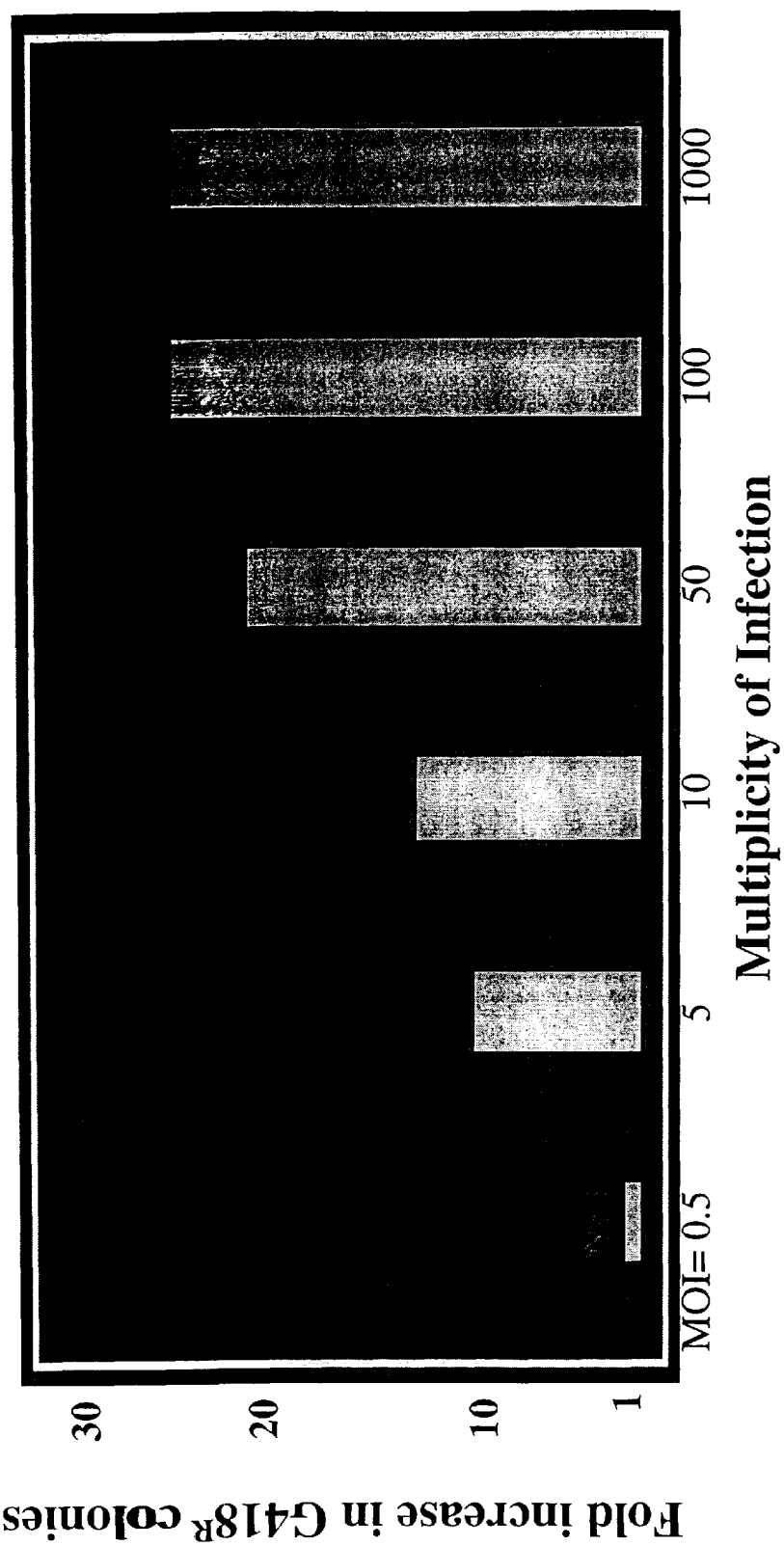
FIG. 20 shows that increasing the multiplicity of infection results in higher retrotransposition frequency. The fold increase in $G418_R$ colonies is graphed versus the multiplicity of infection.

To determine whether increasing the MOI of the adenovirus stage on the target cells would result in a higher retrotransposition frequency, G418-resistant colonies were counted after infection with progressively increasing doses of HDL1.3 neo vector. Up to 25-fold increase in retrotransposition frequency was observed with increasing doses up to a MOI of 100, after which no further increase was observed (FIG. 20).

The foregoing description of the invention has been presented for purposes of illustration and explanation and is not intended to limit the invention to the precise manner of practice described herein. It is to be appreciated therefore, that changes may be made by those skilled in the art without departing from the spirit of the invention and that the scope of the invention should be interpreted with respect to the following claims.

All of the following publications which are cited in the body of the instant specification are hereby incorporated by reference in their entirety.

LITERATURE CITED:

Bilbao, G. et al. (1997). Adenoviral/retroviral vector chimeras: a novel strategy to achieve high-efficiency stable transduction in vivo. FASEB J. 11, 624–34.

Boeke, J. (1997). LINEs and Alus-the polyA connection. Nature Genetics 16, 6–7.

Cannon, P. M. et al.(1996). Murine leukemia virus-based Tat inducible LTR replacement vectors: a new system for anti-HIV gene therapy. J. Virol. 70, 8234–40.

Chakraborty, A. K. et al.(1994). Transmission of endogenous VL30 retrotransposons by helper cells used in gene therapy. Cancer Gene Ther. 1, 113–8.

Clemens, P. R. et al. (1996). In vivo muscle gene transfer of full-length dystrophin with an adenoviral vector that lacks all viral genes. Gene Ther. 3, 965–72.

Engelhardt, J. F. et al. (1993). Direct gene transfer of human CFTR into human bronchial epithelia of xenografts with E1-deleted adenoviruses. Nat.Genet. 4, 27–34.

Feng, Q. et al. (1996). Human L1 retrotransposon encodes a conserved endonuclease required for retrotransposition. Cell 87, 905–16.

Fisher, K. J. et al. (1996). A novel adenovirus-adeno-associated virus hybrid vector that displays efficient rescue and delivery of the AAV genome. Hum. Gene Ther. 7, 2079–87.

Flotte, T. R. et al. (1993). Stable in vivo expression of the cystic fibrosis transmembrane conductance regulator with an adeno-associated virus vector. Proc. Natl. Acad. Sci. USA 90,10613–7.

Flotte, T. R. et al. Am J Respir Cell. Mol. Biol. 11, 517–21.

Gao, G. P. et al. (1996). Biology of adenovirus vectors with E1 and E4 deletions for liver-directed gene therapy. J. Virol. 70, 8934–43.

Gueiros-Filho, F. J. and Beverly, S. M. (1997) Transkingdom transposition of the Drosophila element Mariner within the protozoan Leishmania. Science, 276: 1716–1719.

Haecker, S. E. et al. (1996). In vivo expression of full-length human dystrophin from adenoviral vectors deleted of all viral genes. Hum. Gene Ther. 7, 1907–14.

Halbert, C. L. et al. (1995). Adeno-associated virus vectors transduce primary cells much less efficiently than immortalized cells. J. Virol. 69, 1473–9.

Hattori, M. et al. (1986). L1 family of repetitive DNA sequences in primates may be derived from a sequence encoding a reverse transcriptase-related protein. Nature 321, 625–628.

Hodgson, C. P. et al. (1997). Biosynthetic retrovectoring systems for gene therapy. J. Mol. Med. 75, 249–58.

Hohjoh, H., and Singer, M. F. (1996). Cytoplasmic ribonucleoprotein complexes containing human LINE-1 protein and RNA. EMBO J. 15, 630–639.

Holmes, S. E., Singer, M. F., and Swergold, G. D. (1992). Studies on p40, the leucine zipper motif-containing protein encoded by the first open reading frame of an active human LINE-1 transposable element. J. Biol. Chem. 267, 19765–19768.

Hwang, L. H. S., and Gilboa, E. (1984). Expression of genes introduced into cells by retroviral infection is more efficient than that of genes introduced into cells by DNA transfection. J. Virol. 50, 417–424.

Ivics, Z. et al. (1997). Molecular reconstruction of Sleeping Beauty, a Tc1-like transposon from fish, and its transposition in human cells. Cell 91,501–10

Johnston, K. M. et al. (1997). HSV/AAV hybrid amplicon vectors extend transgene expression in human glioma cells. Hum. Gene. Ther. 8, 359–70.

Kaplan, J. M. et al. (1997). Characterization of factors involved in modulating persistence of transgene expression from recombinant adenovirus in the mouse lung. Hum. Gene Ther. 8, 45–56.

Kingsman, A. J. et al. (1995). Yeast retrotransposon particles as antigen delivery systems. Ann. N.Y. Acad. Sci. 754, 202–13.

Kochanek, S. et al. (1996). A new adenoviral vector: Replacement of all viral coding sequences with 28 kb of DNA independently expressing both full-length dystrophin and beta-galactosidase. Proc. Natl. Acad. Sci. USA 93, 5731–6.

Lieber, A. et al. (1996). Recombinant adenoviruses with large deletions generated by Cre-mediated excision exhibit different biological properties compared with first-generation vectors in vitro and in vivo. J. Virol. 70, 8944–60.

Lucher, L. (1995). Abortive adenovirus infection and host range determinants. In The Molecular Repertoire of Adenoviruses, W. Doerfler and P. Bohm, eds. (Berlin, Heidelberg, New York: Springer), pp. 119–152.

Mann, R. et al. (1983). Construction of a retrovirus packaging mutant and its use to produce helper-free defective retrovirus. Cell 33, 153–159.

Markowitz, D. et al. (1988). A safe packaging line for gene transfer: Separating viral genes on two different plasmids. J. Virol. 62, 1120–1124.

Miller, A. D., and Buttimore, C. (1986). Redesign of retrovirus packaging cell lines to avoid recombination leading to helper virus production. Mol. Cell. Biol. 6, 2895–2902.

Minakami, R. et al. (1992). Identification of an internal cis-element essential for the human L1 transcription and a nuclear factor(s) binding to the element. Nucl. Acids Res. 12, 3139–3145.

Mitani, K. et al. (1995A). Rescue, propagation, and partial purification of a helper virus-dependent adenovirus vector. Proc Natl Acad Sci USA 92, 3854–8.

Mitani, K. et al. (1995B). Gene targeting in mouse embryonic stem cells with an adenoviral vector. Somat. Cell. Mol. Genet. 21, 221–231.

Moran, J. V. et al. (1996). High frequency retrotransposition in cultured mammalian cells. Cell 87, 917–27.

Mulligan, R. (1993). The basic science of gene therapy. Science 260, 926–932.

Parks, R. J. et al. (1996). A helper-dependent adenovirus vector system: removal of helper virus by Cre-mediated excision of the viral packaging signal. Proc. Natl. Acad. Sci. USA 93, 13565–70.

Plasterk, R. H. (1999) Resident aliens: the Tcl/mariner superfamily of transposable elements. Trends Genet. 15, 326–32.

Plasterk, R. H. (1996) The Tc1/mariner transposon family. Curr. Top. Microbiol. Immunol. 204, 125–43.

Parks, R. J., and Graham, F. L. (1997). A helper-dependent system for adenovirus vector production helps define a lower limit for efficient DNA packaging. J. Virol. 71, 3293–8.

Roessler, B. J. et al. (1995). Inhibition of interleukin-1-induced effects in synoviocytes transduced with the human IL-1 receptor antagonist cDNA using an adenoviral vector. Hum. Gene Ther. 6, 307–316.

Sassaman, D. M. et al.(1997). Many human L1 elements are capable of retrotransposition [see comments]. Nat. Genet. 16, 37–43.

Savard, N. et al. (1997). Defective herpes simplex virus type 1 vectors harboring gag, pol, and env genes can be used to rescue defective retrovirus vectors. J. Virol. 71, 4111–7.

Scott, A. F. et al. (1987). Origin of the human L1 elements: proposed progenitor genes deduced from a consensus DNA sequence. Genomics 1, 113–125.

Singer, M. F. et al. (1993). LINE-1: a human transposable element. Gene 135, 183–188.

Soneoka, Y. et al. (1995). A transient three-plasmid expression system for the production of high titre retroviral vectors. Nucl. Acid Res. 23, 628–633.

Swergold, G. D. (1990). Identification, characterization, and cell specificity of a human LINE-1 promoter. Mol. Cell. Biol. 10, 6718–6729.Thrasher, A. J., de Alwis, M., Casimir, C. M., Kinnon, C., Page, K., Lebkowski, J., Segal, A. W., and Levinsky, R. J. (1995).

Generation of recombinant adeno-associated virus (rAAV) from an adenoviral vector and functional reconstitution of the NADPH-oxidase. Gene Ther. 2, 481–5.

Torrent, C. et al. (1994). Analytical study of rat retrotransposon VL30 RNA dimerization in vitro and packaging in murine leukemia virus. J. Mol. Biol. 240, 434–44.

Varmus, H. (1988). Retroviruses. Science 240, 1427–1435.

Weiss, R. et al. (1984). RNA Tumor Viruses: Molecular Biology of Tumor Viruses (Cold Spring Harbor, N.Y.: Cold Spring Harbor Laboratory).

Xiong, Y., and Eickbush, T. H. (1990). Origin and evolution of retroelements based upon their reverse transcriptase sequences. EMBO J. 9, 3353–3362.

Yang, Y. et al. (1995). Cellular and humoral immune responses to viral antigens create barriers to lung-directed gene therapy with recombinant adenoviruses. J. Virol. 69, 2004–15.

Yoshida, Y. et al. (1997). VSV-G-pseudotyped retroviral packaging through adenovirus-mediated inducible gene expression. Biochem. Biophys. Res. Commun. 232, 379–82.

Yoshimoto, T. et al. (1993). Identification of amino acid residues critical for infection with ecotropic murine leukemia retrovirus. J. Virol. 67, 1310–1314.

What is claimed is:

1. A hybrid vector for genetic material delivery comprising a nucleic acid molecule comprising:
   (a) a helper-dependent adenoviral vector region comprising:
      (i) a first and a second inverted terminal repeat, and
      (ii) an adenoviral packaging signal,
      wherein said adenoviral vector region substantially lacks sequences encoding adenoviral structural genes; and
   (b) a retroviral vector region comprising:
      (i) a packaging component region encoding one or more retroviral structural genes,
      (ii) a promoter region operably linked to said packaging component region, and
      (iii) a transfer component region comprising a retroviral packaging signal and a first and a second long terminal repeat, wherein said first and said second long terminal repeats include heterologous promoter sequences;
      wherein transcripts arising from said transfer component region can be packaged into retroviral particles containing proteins encoded by said retroviral structural genes.

2. The hybrid vector of claim 1 wherein said transfer component region further comprises a sequence encoding said genetic material for delivery.

3. The hybrid vector of claim 1 wherein said first and second adenoviral inverted terminal repeats surround said retroviral region.

4. The hybrid vector of claim 1 wherein said retroviral structural genes comprise gag and pol.

5. The hybrid vector of claim 1, wherein said packaging component further comprises at least one promoter.

6. The hybrid vector of claim 1, wherein said first and second long terminal repeats have different sequences and are from a single retrovirus and wherein the two long terminal repeats have been altered to possess minimal sequence homology while maintaining functionality.

7. The hybrid vector of claim 1, wherein said first and second long terminal repeats have different sequences and wherein said first long terminal repeat is from a first retrovirus and the second long terminal repeat is from a second retrovirus.

8. The hybrid vector of claim 5, wherein said first and second long terminal repeats have different sequences and said first long terminal repeat (LTR) has been altered to deleted and replace the endogenous viral LTR promoter/enhancer sequence upstream of the TATA box with an exogenous viral promoter/enhancer sequence.

9. The hybrid vector of claim 1, wherein said first and second long terminal repeats have different sequences and said first long terminal repeat (LTR) has been altered to delete and replace the endogenous viral LTR promoter/enhancer sequence upstream of the TATA box with a cellular promoter/enhancer sequence.

10. The hybrid vector of claim 1, wherein said first and second long terminal repeats have different sequences and said second long terminal repeat (LTR) has been altered to delete the endogenous viral LTR promoter/enhancer sequence upstream of the TATA box to create a self-inactivating (SIN) vector.

11. The hybrid vector of claim 1, wherein said first and second long terminal repeats have different sequences and said second long terminal repeat (LTR) has been altered to delete and replace the endogenous viral LTR promoter/enhancer sequence upstream of the TATA box with an exogenous viral promoter/enhancer sequence.

12. The hybrid vector of claim 1, wherein said first and second long terminal repeats have different sequences and said second long terminal repeat (LTR) has been altered to delete and replace the endogenous viral LTR promoter/enhancer sequence upstream of the TATA box with a cellular promoter/enhancer sequence.

13. The hybrid vector of claim 2 wherein said nucleic acid molecule is encapsidated by one or more helper adenovirus derived proteins for delivery as an adenovirus particle.

14. The hybrid vector of claim 3 wherein said first and second adenoviral inverted terminal repeats comprise adenovirus serotype 2 or adenovirus serotype 5 sequences.

15. The hybrid vector of claim 3 wherein said adenoviral packaging signal is located adjacent to said first inverted terminal repeat.

16. The hybrid vector of claim 4 wherein said retroviral structural genes further comprise env.

17. The hybrid vector of claim 4 wherein said retroviral structural genes are substantially similar to those of a lentivirus or an oncoretrovirus.

18. The hybrid vector of claim 5, wherein said promoter is a retroviral long terminal repeat promoter.

19. The hybrid vector of claim 5, wherein said promoter is a viral or cellular promoter.

20. The hybrid vector of claim 19, wherein said viral promoter is an SV40, cytomegalovirus (CMV), or Rous sarcoma virus (RSV) promoter.

21. The hybrid vector of claim 7, wherein the first retrovirus is selected from the group consisting of murine leukemia virus (MLV), murine sarcoma virus (MSV), and murine stem cell virus (MSCV).

22. The hybrid vector of claim 7, wherein the second retrovirus is selected from the group consisting of MLV, MSV, and MSCV.

23. The hybrid vector of claim 8, wherein said exogenous viral promoter/enhancer sequence is an SV40, CMV, or RSV promoter.

24. The hybrid vector of claim 9, wherein said cellular promoter/enhancer sequence is a ubiquitously expressed cellular promoter/enhancer.

25. The hybrid vector of claim 9, wherein said cellular promoter/enhancer sequence is a tissue-specific or inducible cellular promoter/enhancer.

26. The hybrid vector of claim 24, wherein said ubiquitously expressed cellular promoter/enhancer is a phosphoglycerokinase (PGK) promoter, elongation factor-1 alpha (EF-1a) promoter, or ubiquitin promoter.

27. The hybrid vector of claim 25, wherein said tissue-specific or inducible cellular promoter/enhancer is a mammalian probasin promoter, lactalbumin promoter, GRP78 promoter, or bacterial tetracycline-inducible promoter.

28. The hybrid vector of claim 11, wherein said exogenous viral promoter/enhancer sequence is an SV40, CMV, or RSV promoter.

29. The hybrid vector of claim 12, wherein said cellular promoter/enhancer sequence is a ubiquitously expressed cellular promoter/enhancer.

30. The hybrid vector of claim 12, wherein said cellular promoter/enhancer sequence is a tissue-specific or inducible cellular promoter/enhancer.

31. The hybrid vector of claim 29, wherein said ubiquitously expressed cellular promoter/enhancer is a phosphoglycerokinase (PGK) promoter, elongation factor-1 alpha (EF-1a) promoter, or ubiquitin promoter.

32. The hybrid vector of claim 30, wherein said tissue-specific or inducible cellular promoter/enhancer is a mammalian probasin promoter, lactalbumin promoter, or GRP78 promoter, or the bacterial tetracycline-inducible promoter.

33. A hybrid vector for genetic material delivery comprising a nucleic acid molecule comprising:
  (a) a helper-dependent adenoviral vector region comprising:
    (i) a first and a second inverted terminal repeat, and
    (ii) an adenoviral packaging signal,
    wherein said adenoviral vector region substantially lacks sequences encoding adenoviral structural genes; and
  (b) a retroviral vector region comprising:
    (i) a packaging component region comprising one or more retroviral structural genes which encode retroviral structural proteins,
    (ii) a promoter region operably linked to said packaging component region,
    (iii) an envelope component region comprising one or more envelope genes which encode envelope proteins capable of encoating retrovirus virions, also operably linked to said promoter region of (ii) or operably linked to a separate promoter region,
    (iv) a transfer component region comprising a retroviral packaging signal, a first long terminal repeat having a first sequence, and a second long terminal repeat having a second sequence, wherein said first and second long terminal repeats have different sequences,
  wherein transcripts arising from said transfer component region can be packaged into retroviral particles containing proteins encoded by said retroviral structural genes and encoated by proteins encoded by said envelope genes.

34. The hybrid vector of claim 33, wherein said first and second long terminal repeats are from a single retrovirus and wherein the two long terminal repeats have been altered to possess minimal sequence homology while maintaining functionality.

35. The hybrid vector of claim 33, wherein said first long terminal repeat is from a first retrovirus and the second long terminal repeat is from a second retrovirus wherein said first and second retroviruses are different.

36. The hybrid vector of claim 34, wherein said first long terminal repeat (LTR) has been altered to delete and replace the endogenous viral LTR promoter/enhancer sequence upstream of the TATA box with an exogenous viral promoter/enhancer sequence.

37. The hybrid vector of claim 34, wherein said first long terminal repeat (LTR) has been altered to delete and replace the endogenous viral LTR promoter/enhancer sequence upstream of the TATA box with a cellular promoter/enhancer sequence.

38. The hybrid vector of claim 34, wherein said second long terminal repeat (LTR) has been altered to delete the endogenous viral LTR promoter/enhancer sequence upstream of the TATA box to create a self-inactivating (SIN) vector.

39. The hybrid vector of claim 34, wherein said second long terminal repeat (LTR) has been altered to delete and replace the endogenous viral LTR promoter/enhancer sequence upstream of the TATA box with an exogenous viral promoter/enhancer sequence.

40. The hybrid vector of claim 34, wherein said second long terminal repeat (LTR) has been altered to delete and replace the endogenous viral LTR promoter/enhancer sequence upstream of the TATA box with an exogenous viral promoter/enhancer sequence.

41. The hybrid vector of claim 35, wherein the first retrovirus is selected from the group consisting of murine leukemia virus (MLV), murine sarcoma virus (MSV), and murine stern cell virus (MSCV).

42. The hybrid vector of claim 35, wherein the second retrovirus is selected from the group consisting of MLV, MSV, and MSCV.

43. The hybrid vector of claim 36, wherein said exogenous viral promoter/enhancer sequence is an SV40, CMV, or RSV promoter.

44. The hybrid vector of claim 37, wherein said cellular promoter/enhancer sequence is a ubiquitously expressed cellular promoter/enhancer.

45. The hybrid vector of claim 37, wherein said cellular promoter/enhancer sequence is a tissue-specific or inducible cellular promoter/enhancer.

46. The hybrid vector of claim 44, wherein said ubiquitously expressed cellular promoter/enhancer is a phosphoglycerokinase (PGK) promoter, elongation factor-1 alpha (EF-1a) promoter, or ubiquitin promoter.

47. The hybrid vector of claim 45, wherein said tissue-specific or inducible cellular promoter/enhancer is a mammalian probasin promoter, lactalbumin promoter, GRP78 promoter, or bacterial tetracycline-inducible promoter.

48. The hybrid vector of claim 39, wherein said exogenous viral promoter/enhancer sequence is an SV40, CMV, or RSV promoter.

49. The hybrid vector of claim 40, wherein said cellular promoter/enhancer sequence is a ubiquitously expressed cellular promoter/enhancer.

50. The hybrid vector of claim 40, wherein said cellular promoter/enhancer sequence is a tissue-specific or inducible cellular promoter/enhancer.

51. The hybrid vector of claim 49, wherein said ubiquitously expressed cellular promoter/enhancer is a phosphoglycerokinase (PGK) promoter, elongation factor-1 alpha (EF-1a) promoter, or ubiquitin promoter.

52. The hybrid vector of claim 50, wherein said tissue-specific or inducible cellular promoter/enhancer is a mammalian probasin promoter, lactalbumin promoter, GRP78 promoter, or the bacterial tetracycline-inducible promoter.

* * * * *